(12) United States Patent
Wagner

(10) Patent No.: US 8,125,563 B2
(45) Date of Patent: Feb. 28, 2012

(54) CAMERA CHIP, CAMERA AND METHOD FOR IMAGE RECORDING

(75) Inventor: Christoph Wagner, Koenigsbach-Stein (DE)

(73) Assignee: OBE Ohnmacht & Baumgärtner GmbH & Co. KG, Ispringen (DE)

( * ) Notice: Subject to any disclaimer, the term of this patent is extended or adjusted under 35 U.S.C. 154(b) by 956 days.

(21) Appl. No.: 12/084,712

(22) PCT Filed: Nov. 10, 2006

(86) PCT No.: PCT/EP2006/010790
§ 371 (c)(1),
(2), (4) Date: May 8, 2008

(87) PCT Pub. No.: WO2007/054332
PCT Pub. Date: May 18, 2007

(65) Prior Publication Data
US 2009/0128685 A1    May 21, 2009

(30) Foreign Application Priority Data

Nov. 10, 2005  (DE) .......................... 10 2005 054 465
Jul. 13, 2006   (DE) .......................... 10 2006 033 391
Sep. 7, 2006    (DE) .......................... 10 2006 041 932

(51) Int. Cl.
*H04N 5/222* (2006.01)

(52) U.S. Cl. ...................... 348/370; 348/371

(58) Field of Classification Search .................. 348/370, 348/371
See application file for complete search history.

(56) References Cited

U.S. PATENT DOCUMENTS

| | | | |
|---|---|---|---|
| 6,166,393 A | 12/2000 | Paul et al. | |
| 6,327,374 B1 | 12/2001 | Piironen et al. | |
| 6,452,632 B1 | 9/2002 | Umeda et al. | |
| 7,969,503 B2 * | 6/2011 | Sladen | 348/371 |
| 2004/0183925 A1 | 9/2004 | Raskar et al. | |
| 2004/0183940 A1 | 9/2004 | Raskar | |
| 2005/0254378 A1 | 11/2005 | Wagner et al. | |

FOREIGN PATENT DOCUMENTS

| | | |
|---|---|---|
| EP | 0 898 163 A1 | 2/1999 |
| EP | 1 030 173 A | 8/2000 |
| WO | WO-2004/051186 A | 6/2004 |

OTHER PUBLICATIONS

International Search Report for PCT/EP2006/010790, ISA/EP, mailed Mar. 30, 2007.
International Preliminary Report on Patentability with annexes and their translation, IPEA/EP, completed Feb. 22, 2008.

(Continued)

*Primary Examiner* — William Choi
(74) *Attorney, Agent, or Firm* — Harness, Dickey & Pierce, P.L.C.

(57) ABSTRACT

The invention relates to a camera chip (C) for image acquisition. It is characterized in that pixel groups (P1, P2, . . . ) may be exposed at different times with the aid of shutter signals (S1, S2, . . . ).

8 Claims, 39 Drawing Sheets

OTHER PUBLICATIONS

Nayar, S. K. et al: "Adaptive dynamic range imaging: optical control of pixel exposures over space and time," Proceedings of the Ninth IEEE International Conference on Computer Vision. (ICCV). Nice, France, Oct. 13-16, 2003, International Conference on Computer Vision, Los Alamitos, CA: IEEE Comp. Soc, US, vol. vol. 2 of 2. Conf. 9, Oct. 13, 2003, pp. 1-9, XP010662526, ISBN: 0-7695-1950-4, the whole document.

Smith, et al: "Dynamic photometric stereo-a new technique for moving surface analysis," Image and Vision Computing, Buildford, GB, vol. 23, No. 9, Sep. 1, 2005, pp. 841-852, XP005006117, ISSN: 0262-8856, the whole document.

Woodham, R. J. Ed—Institute of Electrical and Electronics Engineers: "Determining Surface Curvature With Photometric Stereo," Proceedings of the International Conference on Robotics and Automation. Scottsdale, May 15-19, 1989 Washington, IEEE Comp. Soc. Press, US, vol. vol. 1, May 15, 1989, pp. 3 6-42, XP000047432, ISBN: 0-8186-1938-4, the whole document.

* cited by examiner

CAMERA CHIP, CAMERA AND METHOD FOR IMAGE RECORDING

CROSS-REFERENCE TO RELATED APPLICATIONS

This application is a 371 U.S. National Stage of International Application No. PCT/EP2006/010790, filed Nov. 10, 2006. This application claims priority to German Patent Applications No. 10 2005 054 465.7, filed Nov. 10, 2005, No. 10 2006 033 391.8, filed Jul. 13, 2006, and No. 10 2006 041 932.4, filed Sep. 7, 2006. The disclosures of the above applications are herein expressly incorporated by reference.

FIELD

The invention relates to a camera chip for image acquisition, an electronic camera, a method for optical shape capture, a method for acquiring a number of images, a method for acquiring a number of images using multiple cameras, as well as a method for acquiring a number of images.

BACKGROUND

There are already a large number of measurement principles today by means of which it is possible to capture the three-dimensional shape of objects. Examples include the principles of triangulation (laser light section method, stripe projection, stereo method, photogrammetry, shape from shading), interferometric methods (laser interferometry, white light interferometry, holographic methods), and runtime methods (high-frequency modulation of the light source). All of these methods have in common the fact that multiple camera images must be acquired in order to produce one single 3-D image from them. In the case of most of these methods, it is not possible for these images to be acquired at the same time. In contrast, conventional photographic 2-D images are captured with only one image. This applies in particular to image capture in industrial image processing as well.

The principal difficulty lies in the fact that the use of optical 3-D sensors requires multiple camera captures by its nature. This lies in the fact every 3-D sensor must determine three unknowns for each point of the object to be measured:
- the location of the test specimen point, referred to in the following as "shape"
- the local reflectivity of the test specimen, referred to in the following as "texture" (black/white)
- the local brightness of the ambient light at each point As a rule, three equations are also necessary to determine three unknowns; in terms of 3-D, these are the three camera images with the local brightness of the test specimen, with the three camera images being acquired using three different lighting situations. This is not necessary in the case of the 2-D methods because here only the sum of all influences, e.g., of shape, texture, and ambient light, is ever reproduced in one image.

The number of unknowns is reduced to two unknowns insofar as it is possible for all ambient light to be shaded off. In this case, only two images with two different lighting situations are necessary to detect the 3-D shape of the test specimen.

Even in 3-D methods, there are approaches that allow all of the necessary information to be attained using one single camera image. One such method is spatial phase shifting. In its application, it is limited to interferometry and stripe projection. In this method, the various lighting situations are realized using an interference pattern or a stripe pattern that has regions of different lighting intensities. Therefore, it is possible to detect three different lighting situations at three neighboring picture elements, from which the three unknowns may then be calculated. However, this method cannot be applied to the shape from shading method, in particular not for photometric stereo or photometric deflectometry (see WO2004051186, DE102005013614) or for runtime methods because, in this case, an object is lit from different directions at different times and thus a simultaneous recording of multiple lighting situations is not possible.

However, for many applications, in particular for applications in industrial image processing, it is important for all image information to be recorded simultaneously or virtually simultaneously. Only in this manner is it possible for test specimens in motion to be measured and analyzed without blurring from movement. For this purpose, the exposure time of a camera is reduced to a minimum or a flash is selected. The cameras are equipped with a so-called electronic shutter in order to control the exposure time. All picture elements (pixels) of the camera chip are connected simultaneously in a photosensitive manner for a predetermined time. Typical exposure times range from a few milliseconds to several microseconds. The process of reading the camera chip occurs after exposure. Here, exposure may occur much more quickly than reading, which normally takes several milliseconds. Therefore, an image acquisition period is composed of exposure and reading the cameral chip. Here, the duration of the image acquisition period is determined by the reading time, which takes substantially longer than exposure. By virtue of the long image acquisition period, the refresh rate, i.e., the number of images that may be recorded per second, is reduced. The refresh rate is therefore also determined by the reading time. Specially designed and expensive high-speed cameras which, for example, are able to record a few thousand images per second, represent the exception. Thus, the optical 3-D method has a decisive disadvantage. Instead of an exposure time of a few microseconds, a series of, for example, four images (for example, 20 ms each per image acquisition) requires an acquisition time of 80 ms, over 1000 times that of the 2-D method.

SUMMARY

The object of the invention is therefore to create an optical 3-D sensor that allows a significantly shorter acquisition time. This sensor is referred to as a "single-shot 3-D sensor."

The further object of the invention is to create a camera and method for optical shape capture requiring only a very short exposure time.

In order to attain the objects mentioned above, a camera chip, a camera, and a method are created that are generally suitable for optical 3-D processes and allow several images to be acquired within the shortest time.

DRAWINGS

The invention is described in greater detail below with reference to the drawings, which show:

FIG. 1a a basic sketch of a camera chip with a number of pixel groups;

FIG. 1b an exemplary progression of shutter signals over time;

FIGS. 2a to d a basic sketch of photometric deflectometry with four shutters and four illuminations;

FIG. 2e a basic sketch of photometric stereo with four shutters and four illuminations;

FIGS. 3a to d a basic sketch of the stripe projection method with four shutters and four illuminations;

FIG. 3e a basic sketch of interferometry with four shutters and four illuminations;

FIG. 4a a schematic depiction of a partial region of a modified camera chip;

FIG. 4b an exemplary progression of shutter signals over time;

FIG. 5 an exemplary embodiment of a camera chip C;

FIG. 6 a diagram to show control of shutter and illumination signals over time;

FIG. 7 a modified exemplary embodiment of a camera chip C;

FIGS. 8a to d a basic sketch of photometric deflectometry in the case of linear movement by the test specimen with four illuminations and four camera chip lines;

FIG. 8e a basic sketch of photometric deflectometry in the case of rotational movement by the test specimen with four illuminations and four camera chip lines;

FIG. 9a upper diagram: progression over time of four active camera chip lines as a function of the location on the surface of the test specimen; lower diagram: corresponding active illuminations;

FIG. 9b a schematic depiction of a memory area for storing read camera chip areas;

FIG. 10a a modified schematic depiction for storing read camera chip areas in a memory area;

FIG. 10b a modified diagram for the purpose of clarifying the temporal and spatial progression of the activation of camera chip lines in acquiring various images; lower diagram: corresponding active illuminations;

FIG. 10c a schematic depiction for the purpose of storing read camera chip areas in a memory area;

FIG. 11a a basic sketch of photometric stereo in the case of linear movement by the test specimen;

FIG. 11b a basic sketch of photometric stereo in the case of rotational movement by the test specimen;

FIGS. 12a to d a basic sketch of the stripe projection method in the case of linear movement;

FIG. 12e a basic sketch of the stripe projection method in the case of rotational movement by the test specimen;

FIG. 13a a basic sketch of interferometric evaluation in the case of rotational movement by the test specimen;

FIG. 13b a basic sketch of interferometric evaluation in the case of linear movement by the test specimen;

FIG. 14a a basic sketch of the white light interferometry method in the case of linear movement by the test specimen;

FIG. 14b a basic sketch of the white light interferometry method in the case of rotational movement by the test specimen;

FIG. 15 an arrangement of two cameras in a vertical fashion over a plane in which a test specimen has been arranged;

FIGS. 16a to d a modified basic sketch of photometric deflectometry in the case of rotational movement by the test specimen with four illuminations and one line, and FIG. 16e a basic sketch of photometric deflectometry with a highly light-sensitive line camera.

DETAILED DESCRIPTION

According to the invention, a specially designed camera chip C of an electronic camera K is used for image acquisition, for example, using CCD or CMOS technology.

FIG. 1a shows a schematic section of a camera chip C with multiple pixels P. Here, individual pixels P are combined into pixel groups P1, P2, P3, and P4. These pixel groups P1 to P4 are activated via various electronic shutter signals S1, S2, S3, S4, i.e., they are connected in a light-sensitive manner. Here, precisely one shutter S1 to Sn is assigned to each pixel group P1 to Pn. Individual pixels P are arranged at a distance $\Delta x$ and/or $\Delta y$ from one another. This distance is preferably selected to be very small in order to achieve full coverage by the distribution of the pixels P, such that the yield for the camera chip area is large.

In the following figures, only a few pixels P or pixel groups P1 to Pn of the camera chip C are shown. However, each respective pattern must be imagined as continuing in the horizontal and vertical directions until the desired number of pixels P, for example, two megapixels, has been achieved. Shutters Sn are assigned to these pixels. An electronic shutter is understood to mean an illumination control that is able to connect a pixel P for a certain time in a light-sensitive manner or in a non-light-sensitive manner. In this manner, it is possible for neighboring pixels P of various pixel groups P1 to Pn to be exposed with different images in rapid succession over time. The camera chip C will not be read until all pixel groups P1 to Pn have been exposed one after the other. Therefore, upon reading, there are as many images in partial regions of the camera chip C as pixel groups that were connected one after the other in a light-sensitive fashion by shutters. Because the reading process determines the image period, i.e., the sum of the exposure and reading times, and thus the refresh rate, i.e., the number of images acquired per second, it is possible in this manner for several images to be acquired within the shortest period of time without a needing to wait for a comparably protracted reading process after each exposure process.

FIG. 1b shows a progression over time of the various shutter signals, with t signifying the time axis. The shutter signals are shown as right-angle pulses over a certain time interval $\Delta t$. The light sources designated as illuminations must be synchronized with the shutter signals, for example, illumination B1 with shutter S1, illumination B2 with shutter S2, etc. For example, the shutter S1 is actively connected for 20 microseconds, then shutters S2, S3, S4 for 20 microseconds each. After only 80 microseconds, four images are present in four neighboring pixels that were captured at different times and with different illumination conditions and that were acquired in accordance with a known 3-D process, for example, shape from shading, and are then able to be read from the camera chip. In particular, the photometric stereo method and photometric deflectometry method are possible in an advantageous fashion with four illuminations (see WO2004051186, DE102005013614). Theoretically, two illuminations are also sufficient to produce a 3-D image. However, it is preferable for four illuminations to be used because, in this case, the acquisitions are less sensitive to disruptions, for example, deviations in the arrangement of the illuminations or brightness tolerances.

FIGS. 2a to 2d show an application for photometric deflectometry with four illuminations B1 to B4. Photometric deflectometry is a method of optical 3-D measurement. It represents a combination of the photometric stereo method and deflectometry. This method is suitable for reflective, glossy, and matte surfaces. For this purpose, an appropriately shaped diffuser, for example, a hemisphere, is illuminated from various directions. This diffuser in turn illuminates the test specimen. One camera image is recorded for each illumination direction. The analysis of the various images occurs in a manner similar to the photometric stereo method. The method is described in detail in WO2004051186.

In the upper portion of each of FIGS. 2a to 2d, a side view of the structure is shown. A camera K is oriented on the test specimen G in a vertical manner through an opening in the diffuser S. The field of vision of the camera K oriented on the test specimen G is implied here by two lines L1 and L2. The circles labeled with B1 to B4 represent the illuminations. The illuminations B1 and B2 are arranged in an offset manner inside the image plane, which is not discernible in the side view. The illumination currently shown as being light is the active illumination.

In the lower portion of each of FIGS. 2a to 2d, a top view of the structure may be seen. In this view, the camera K is not shown in order to allow a view of the test specimen G. The circle that is currently shown as being light is the active illumination. A pixel pattern section A of a camera chip C has been projected onto the test specimen G in order to clarify the synchronization of the individual illuminations B1 to B4 with the camera chip C. The light diamonds represent individual pixels P of a pixel group Pn, which are activated by a shutter Sn, i.e., connected in a light-sensitive fashion. The lower edge of the diffuser S is also visible.

As may be seen from the lower portion of FIG. 2a, initially the illumination B1, the pixel group P1, and the shutter S1 are active. After a predetermined exposure time, the illumination switches to B2, i.e., the illumination B1 is switched off and B2 is switched on. Correspondingly, the pixel group P2 and the shutter S2 are active, as is shown in FIG. 2b. FIGS. 2c and 2d show how the cycle correspondingly continues with illuminations B3 and B4.

FIG. 2e shows an application for photometric stereo. As may be seen from this figure, no diffuser is used in this method, and the illuminations B1 to B4 are arranged at a greater distance from the test specimen. Otherwise, we refer to the description of the previous figures. Again, the light illuminations, shown as circles, are activated. For reasons of simplicity, only the active illumination B1 of the first cycle is shown; the other illuminations follow in an analogous manner.

FIGS. 3a to 3d show the application to the stripe projection method with four different illumination situations that are produced by a stripe projector that projects a stripe pattern onto the test specimen G. In the upper portion of the figures, a side view of the structure is again shown. Here, a camera K is oriented in a vertical fashion on a test specimen G, and the field of view of the camera K is implied by the lines L1 and L2. Next to the camera K to its left, the stripe projector is implied. The projection field of the stripe projector is implied here by the lines L3 and L4. The stripe projector is arranged at an angle that does not equal 90° to the test specimen.

In each of the lower portions of FIGS. 3a to 3d, a top view of the structure is shown. The camera K and the stripe projector are not shown here; only the field of view of the camera in the form of a pixel pattern section A of a camera chip C as well as the stripe pattern produced by the stripe projector have been partially projected onto the test specimen G in order to clarify the synchronization of the illumination situation Bn with the camera chip C. The pixel section A of the camera chip C has individual pixels P. The light diamonds represent the pixels P of a pixel group Pn that is activated by a shutter Sn, i.e., connected in a light-sensitive manner.

The sinusoidal stripe patterns shown here (other patterns are possible) originate from an original pattern by phase shifting by 0°, 90°, 180°, and 270°. As is implied by the arrow 1, upon a phase shift, the pattern migrates to the left by a certain angle, i.e., the stripes of light move.

FIG. 3a shows a stripe pattern in the phase position of 0° that is being projected onto a test specimen G. The pixel group P1 and the shutter S1 are active here. After a phase shift of 90°, the pixel group P2 is connected in a light-sensitive manner via the shutter S2, as is shown in FIG. 3b. The above applies correspondingly for phase shifts by 180° and 270° for pixel groups P3 and P4, as is shown in FIGS. 3c and 3d. Thus, each pixel group records a different illumination situation by virtue of the shifting of the stripe pattern.

Stripe patterns with other stripe periods are also conceivable; a greater number of pixel groups is advisable in such a case.

Other applications, for example, to the method of interferometry, white light interferometry, and other methods of optical shape capture are also conceivable.

FIG. 3e shows the application of the method to laser interferometry. The arrangement has a laser L, a beam splitter T (semipermeable mirror), a fixed mirror P, a test specimen G, and a camera K, as well as two lenses I1 and I2. The beam emitted by the laser L having a particular wavelength is deflected by the beam splitter T on one side onto the surface of the test specimen G and on the other side onto the mirror P. The beam is reflected by the surface of the test specimen G and it strikes the beam splitter again. The beam striking the mirror P is also reflected back to the beam splitter. In the beam splitter, the two beams meet again and overlap. The camera K is structured in such a way that the overlapping light strikes it. By virtue of the different lengths of the paths that the light travels to the test specimen and the fixed mirror P, a difference between the light paths of 0, 1, 2, 3, 4, . . . times the wavelength of the laser, with the overlay (interference) in the beam splitter, the brightness (constructive interference) results, and in the case of a difference of 0.5, 1.5, 2.5, . . . times the wavelength of the laser, the darkness (destructive interference) results. From the distribution of brightness and darkness (interference stripes), the shape of the test specimen G may be suggested.

In the following, a displacement in the x direction refers to a horizontal displacement and a displacement in the y direction refers to a vertical displacement, relative to plane of the image.

FIG. 4a shows a schematic section of a camera chip C with four pixel groups P1 to P4. Grey shaded areas are visible in the figure, but these areas are for illustration purposes only and do not have any technical effect. One pixel P each of each pixel group Pn is located in such a grey area. In the upper left-hand grey area are the pixels P1 to P4. Pixels P1 to P4 are also provided in the upper right-hand, lower left-hand, and lower right-hand grey areas. A first pixel group includes all pixels P1 of all grey areas, a second pixel group includes all pixels P2 of all grey areas, and so on. All pixels P of a pixel group P1 to P4 are simultaneously activated via a shutter S1 to S4. As may be seen from FIG. 4a, the location of the four different pixel groups P1 to P4 slightly from pixel group to pixel group. For example, the pixel group P2 is displaced by a pixel distance Δx in the x direction relative to the pixel group P1. Correspondingly, the pixel group P3 is displaced by a pixel distance Δy in the y direction relative to the pixel group P1 and the pixel group P4 is displaced by a pixel distance Δx in the x direction and by a pixel distance Δy in the y direction relative to the pixel group P1. However, it is desirable for all four of the images captured by the pixel groups P1 to P4 to be shown in a common pixel grid. The middle point M of neighboring pixels P, i.e., pixels in a grey shaded area, lends itself to being used as a point of reference.

Alternately, another reference point may be selected, for example, the location of the pixels P from the group P1 or P2 etc. By interpolation of the measurement values of the pixels P from pixel group P1 also designated as grey values, values are calculated using reference points, for example, using the reference point M, and in the same manner for all remaining pixel groups P2 to P4. Interpolation is also possible for a different number of pixel groups. For reasons of time, this calculation may be conducted in an advantageous fashion on hardware of the camera designed for this purpose, as opposed to on a connected computer.

Alternately, it is also possible to provide other time patterns. FIG. 4b shows the progression over time of four shutters S1 to S4. The shutter signals that connect the individual pixel groups Pn in a light-sensitive manner are depicted as right-angle pulses over a certain time interval Δt. The time axis is designated by t. For example, first the pixel groups P1 to P4 are exposed one after the other for Δt=2 microseconds and this process is repeated ten times until a total exposure time of 20 microseconds has been attained. Thus, the temporal difference between exposures of consecutive pixel groups is only 2 microseconds. The selection of times and number of repetitions represents only an example and may be varied virtually arbitrarily. For example, sinusoidal or otherwise modulated shutter signals may be used. The advantage of shorter exposure times is that the test specimen has continued to move a shorter distance between the exposure of the individual pixel groups Pn. Although the total exposure time for each pixel group Pn is the same, the amount of local blurring between the pixel groups Pn caused by the moving test specimen is lower.

Alternately, a smaller or larger number of pixel groups may also be selected. FIG. 5 shows a schematic section of a camera chip C with a structure of the simplest case, namely the use of only two pixel groups P1 and P2. Again, one pixel P each of a pixel group P1 is adjacent to a pixel P of the other pixel group P2, as is implied again in FIG. 5 by the grey shaded areas. The connection lines clarify that each pixel group P1 and P2 is activated by two different shutters S1 and S2. By virtue of the similarity to camera chips in interlaced mode (line skip), such an interlaced mode camera chip could be modified according to the invention by a few changes. The difference from the interlaced mode lies in the fact that the even and odd lines there are exposed with a time difference corresponding to a refresh frequency or half of a refresh frequency. This means that the shutters that activate, for example, the odd lines, do not become active until the image acquired from the even lines has been read. Conversely, the shutter that controls the even lines does not become active until the image from the odd lines has been read. The camera chip C must therefore be modified in such a way that the shutter time does not equal the full image period, i.e., waits for exposure and reading, but rather waits only for the exposure time and, directly after the exposure of the even or odd lines, the corresponding other shutter connects the other lines in a light-sensitive fashion. According to the invention, the time difference is therefore only the duration of the shutter time, which may easily be shorter by a factor of 1000 than the total image period with exposure and reading.

Alternately, an existing interlaced camera chip C may be used in combination with a special timed control of illumination. FIG. 6 shows an exemplary progression of the shutter signals S1, S2 that connect the pixel groups P1 and P2 in a light-sensitive manner and the corresponding activation of the illuminations B1 and B2 over time t. The shutter signals as well as the active illuminations are depicted as right-angle pulses. The scale of the time axis t does not correspond to the scale of the other figures having time axes. The illumination B1, for example, is activated for a short time shortly before the end of the shutter time of pixel group P1. As soon as the exposure of the pixel group P2 begins, the illumination B1 is deactivated and the illumination B2 is also activated for a short time. The time in which the illuminations are activated may preferably be much shorter than corresponding to the image period, i.e., the total of illumination time and reading time, for example, from several microseconds to a few milliseconds. It is crucial here that the different illumination situations B1 and B2 be recorded one directly after the other. Here, the pixel group P1 records the test specimen G under the illumination situation B1 and the pixel group P2 records the test specimen G under the illumination situation B2. After both pixel groups P1 and P2 have been exposed one after the other, the camera chip C may be read.

Alternately, in the case of a new camera chip design, as already mentioned above, a greater number of pixel groups P1 to Pn may be formed. The numbers 2×2=4, as shown in FIG. 1a, as well as 3×3=9, 4×4=16, etc. are particularly suitable because neighboring pixels P may be combined into a square surface and the same interpolation distances result in the x direction and y direction, which simplifies calculation of reference points due to symmetry.

FIG. 7 shows a section of a camera chip C with 3×3 pixel groups P1 to P9. Again, neighboring pixels P of different pixel groups P1 to P9 are shaded in grey. For reasons of simplicity, the lines for shutters S1 to S9 are not shown.

Alternately, for a simpler production of the camera chip C, it may also be advisable not to arrange pixel groups with their own shutter signal in a square fashion, but rather in groups of 2×1, 3×1, 4×1, etc. pixels, i.e., in lines. The advantage of such an arrangement lies in the fact that each line of the camera chip C is assigned to precisely one shutter signal and the connection layout of the camera chip C has a simple structure. Such an arrangement for 2×1 pixel groups P1 and P2 is shown in FIG. 5. The arrangement would be expanded correspondingly for 3×1, 4×1, etc. pixel groups.

An additional alternative lies in a rectangular arrangement of the pixel groups Pn, for example, 2×3, 3×4, or other side ratios. The arrangement of eight pixel groups P1 to P8 in a 3×3 grid is also conceivable, with one grid point, for example, the middle grid point, remaining unused; a reference point, for example, could be arranged there too which the surrounding pixels P of the individual pixel groups P1 to P8 are interpolated. In general, other arrangements, even asymmetrical ones, are conceivable as well.

The majority of the variant solutions discussed above assume the creation of a novel camera chip design or the modification of an existing camera chip design. The only exception is the use of an interlaced camera chip C in which even and odd lines are already exposed at different points in time. The illumination activation must then only be adapted accordingly, as is shown in FIG. 6.

Additional variant solutions will be introduced below that do not require any changes to the camera chip design.

Method for Matrix Cameras or Line Cameras with Multiple Lines

Using a common, flat matrix camera chip that cooperates with only one shutter S1, multiple camera images (number n) should be recorded in a very close succession, in other words, much more quickly than several milliseconds. Initially, this appears to be a contradiction in terms because such short image periods and the resulting high refresh rate cannot be achieved with a conventional method of use of a matrix camera chip.

According to the invention, the specimen to be tested is initially lit with a first illumination B1 of a total of n illuminations, the entire camera chip C is exposed with the aid of the shutter S1, and only one partial region of the camera chip C is read, in particular a certain number of lines Z1 to Zn or columns of the camera chip C or parts thereof. In the following, we will discuss only lines; however, the same always applies to columns and parts of lines or columns. One or more lines are read, preferably as many as there are images that must be captured with different illuminations, or a multiple thereof. In a special case, one or more illuminations may be dark and/or one or more illuminations may be identical.

FIGS. 8a to 8d show in their top portion a side view of a structure for photometric deflectometry. Equivalent parts have been assigned the same reference characters; in this regard, we refer to preceding figures. Again, the light circles represent the active illuminations, the dark circles represent the inactive illuminations. The test specimen G with a mark X, which moves in a synchronized fashion with the test specimen G in the direction of the arrow 1, is also discernible. The four regions L5 to L8 designate the field of view of the camera on the test specimen G, with each region L5 to L8 standing for one line Z1 to Z4 of the camera chip C.

The lower portion of FIGS. 8a to 8d shows a top view of the structure. The camera K is not shown; only a pixel grid section A of the camera chip C is partially projected onto the test specimen G in order to clarify how the camera chip C is synchronized with the illuminations B1 to B4.

First, as is shown in FIG. 8a, the illumination B1 is activated and lines Z1 to Z4 are exposed and read. A mark X on the test specimen G, which has been selected by way of example, is in motion at this point in time in the region of the line Z4. Then, a shift occurs to a second illumination B2, and another partial region of the camera chip C is read, preferably the same region that recorded the previous illumination situation with B1. The test specimen G, and with it the mark X, has in the meantime moved farther by a certain distance. The mark x is now, for example, located in the region of the line Z3, as is shown in FIG. 8b.

This sequence repeats, as is shown in FIGS. 8c to 8d, until a number of illuminations n has been achieved. Then the next series of n illuminations and reading processes follows until a desired number of repetitions has been reached. Here, the test specimen G is in motion relative to the camera, such that the surface of the specimen or parts of it are covered over. This motion may occur in various manners, for example, motion in a straight line at a constant speed and in a constant direction. For rotationally symmetrical specimens whose coatings are to be tested, a rotation around their symmetrical axis at a constant rotational speed recommends itself.

Another variant, which is not shown here, is a movement of the test specimen G in which, in addition to rotation, a simultaneous feeding of the test specimen G along the rotational axis occurs. Thus, one point on the surface of the test specimen G described a helical path. Here, the lines of the camera chip C must be configured in such a way that they are situated perpendicular to the helical line. One advantage of this movement is that even long cylindrical components may be completely captured within several rotations. However, multiple individual test specimens may also be arranged one after the other and, in this manner, continually tested.

FIG. 8e shows by way of example the structure for the photometric deflectometry method; however, in contrast to FIGS. 8a to 8d, this figure shows a test specimen G that is rotating in the direction of the arrow 1. Again, cones L5 to L8 imply the field of view of the camera and/or the recording locations of the individual lines Z1 to Z4 of the camera chip C on the test specimen G.

From capture to capture, the test specimen G continues to move along a certain route or by a certain rotational angle. The speed, rotational speed, time of capture, and/or time of reading are advantageously selected such that the test specimen G moves from capture to capture relative to the camera by a pixel distance or a whole-number multiple thereof. This may be achieved, for example, by an encoder coupled with the motion, in particular a rotational encoder, that specifies the image capture time point and reading time point correspondingly such that tolerances of the motor do not have any negative effects.

In the upper portion of FIG. 9a, the location of the test specimen G, which is being captured by lines Z1 to Z4, is shown (vertical axis) as a function of time (horizontal axis).

The lower portion of FIG. 9a shows which illumination B1 to B4 is active. The illuminations are activated one after the other; at the same time, lines Z1 to Z4 are connected in a light-sensitive manner. After each illumination process, lines Z1 to Z4 are read.

Over time, lines Z1 to Zn gradually capture various locations with regard to the test specimen G. The number of lines and the number of illuminations were selected by way of example at n=4. Other numbers n are possible as well.

The image areas that have been read, in this case lines Z1 to Z4, are transmitted to an arithmetic unit R and stored in a memory there, with said storage occurring according to a certain pattern.

FIG. 9b shows a schematic depiction of such a memory pattern that is arranged in a memory area depicted in a highly abstract manner. The individual boxes Z1 to Z4 represent the measurement values that the lines Z1 to Z4 of the camera chip C recorded from the respective surface section of the test specimen G with a certain illumination situation. The storage order of the measurement values is organized by illuminations. First, therefore, lines Z1 to Z4 are illuminated with B1 and stored in the memory, then lines Z1 to Z4 are exposed with illumination B2 and stored one line below in the memory. This process repeats for all four illuminations. Then the storage process begins again subsequent to the first storage. Here, in each grey shaded memory region, an image results that was recorded with illuminations B1, B2, B3, and B4, with the recorded surface of the test specimen G running in the direction of the arrow O. In the figure, the respective illumination B1 to B4 with which the test specimen was illuminated is given under each column. Lines Z1 to Z4 are stored in the memory in such a way that the same mark X on the surface of the test specimen G is arranged in a horizontal row. Here, so-called corresponding lines result that correspond to the same location on the surface of the test specimen with different illumination situations. One example of corresponding lines in the case of illuminations B1 to B4 is designated with K in the figure. In the case of this example, "corresponding" means that the line Z4 under illumination B1 shows the same region of the test specimen G, for example, the mark X, as line Z3 under illumination B2, Z2 under B3, and Z1 under B4. Thus, pixel-identical data, i.e., data of the same surface region, are present for each illumination B1 to B4. This is a particular advantage because it eliminates the need for interpolation between intermediate values. This leads to less laborious calculations and less expenditure of time. Moreover, errors that would otherwise occur during interpolation can be avoided. Such errors particularly occur in the case of sharp brightness transitions in the image, area that are often of great interest.

The lines that were recorded with different illuminations are arranged one next to the other horizontally in FIG. 9b. This two-dimensional depiction is for the sake of clarity, so that corresponding lines may be shown in the most comprehensible manner possible. Naturally, these memory regions in the storage medium may also be arranged in an alternate manner. For example, the arrangement of the lines in the memory may also have a linear concept. In the simplest case, the lines of the camera are stored one directly after the other in the memory in a linear fashion and corresponding lines are assigned with reference to their distance from one another in the memory. All of these different arrangements in the memory should be viewed as equivalent to the memory arrangement shown, as long as it is possible to designate corresponding memory regions. This also applies to subsequent figures that show the memory.

As an alternative to FIGS. 9a and 9b, the displacement may also be a multiple of the pixel distance, for example, twice the pixel distance. In this case, eight lines each must be read. The arrangement in the memory of the arithmetic unit is then preferably selected as in FIG. 10a, which also shows a schematic depiction of a memory pattern. Again, the individual boxes Z1 to Z8 represent the information that the lines Z1 to Z8 of the camera chip C have recorded of the respective surface section of the test specimen G with a particular illumination situation. The recorded surface of the test specimen G runs in the direction of the arrow O.

The reading times achieved in this method are typically lower by a factor of 100 to 1000 than reading the entire matrix camera chip by virtue of the fact that only partial regions of the matrix camera chip are read. The factor of 100 results in cases in which only 4 lines are read instead of 400; the factor of 1000 results when only 2 lines are read instead of 2000. For this reason, the variant for n=2 is of particular interest.

The upper portion of FIG. 10b shows the location on the surface of the test specimen G (vertical axis) that the two lines Z1 and Z2 of the camera chip C record as a function of time (horizontal axis).

The lower portion of FIG. 10b shows illuminations B1 and B2, depicted as right-angle pulses, which are activated in an alternating fashion. The test specimen continues to move, as may be seen from the upper portion of FIG. 10b, by a line distance of the camera chip C, lines Z1 and Z2 are again connected such that they may be exposed, and the second illumination B2 is activated.

FIG. 10c shows the corresponding memory pattern in a highly schematic memory when two lines Z1 and Z2 are used. Again, information is shown regarding the surface of the test specimen G in the boxes Z1 and Z2. The surface of the test specimen G again moves in the direction of the arrow O. A corresponding line K clarifies that the same surface regions of the test specimen G that were recorded with different illuminations B1 and B2 are arranged one next to the other in a horizontal row.

Additional exemplary applications are shown in FIGS. 11a to 14b. FIG. 11a shows an application of the method to the photometric stereo method and a linear movement of the test specimen G, which moves in the direction of the arrow 1. In contrast to photometric deflectometry, the diffuser has been eliminated here and the illuminations B1 to B4 are arranged at a greater distance from the test specimen G. In the upper portion of FIG. 11a, the field of view of the camera K is designated by regions L5 to L8, which represent individual lines of the camera chip C. The same parts are designated using the same reference characters; in this regard, we refer to the preceding figures.

FIG. 11b shows the method applied to the photometric stereo method in combination with a rotational movement by the test specimen G, which rotates around the rotational axis 3 in the direction of the arrow 1.

In FIG. 12a, the method according to the invention is applied to the stripe projection method, which is known per se, and a linear movement by the test specimen G.

In the upper region of FIG. 12a, a side view of the structure may be seen. The field of view of the camera K is designated by regions L5 to L8, which represent individual lines of the camera chip C. A stripe projector SP illuminates a region of the test specimen G with a stripe pattern whose area is designated by the lines L3 and L4. Preferably, the stripe projector provides illumination with a sinusoidal modulation of illumination intensity depending on the location on G. The test specimen G preferably moves in a linear and even fashion in the direction of the arrow 1.

In the lower portion of FIG. 12a, a top view of the structure may be shown. Here, the test specimen G, the strip pattern projected thereon, and a projection of the field of view of lines Z1 to Z4 of the camera chip C are shown.

FIG. 12a shows how a mark X is initially located in the region of the line Z4, then in the region of the line Z3 according to FIG. 12b, then in region of the line Z2, and in the region of the line Z1, as is shown in FIGS. 12c and 12d.

In the case of stripe projection, the stripe pattern may be varied from time segment to time segment in its phase position and stripe distance (this corresponds to the different illuminations B1 to Bn); however, this is advantageously not necessary. The movement of the test specimen alone ensures that a mark X will be located in different regions of the stripe pattern at different points in time (in different phase positions of the stripe pattern). Advantageously, the stripe distance is selected such a way that, after n movement steps, precisely one stripe period, i.e., one light stripe and one dark stripe, will be crossed. In the present example, n=4. Thus, the mark X is recorded in line Z4 with a phase position of 0° (B1), in Z3 with a phase position of 90° (B2), in Z2 with 180° (B3), and Z1 with 270° (B4). This motion therefore automatically creates an appropriate phase shift that must first be laboriously produced in other methods.

The particular advantage of the method according to the invention therefore lies in the fact that an extremely simple and cost-effective projector may be used with a static, unchanging stripe pattern and a high degree of stripe contrast. In this case, the temporal succession of the n illuminations is replaced by the spatial progression of n illuminations. Each phase position of the illumination, for example, 0°, 90°, 180°, 270°, which occur one next to the other spatially, corresponds to an illumination Bn. It is possible for one or more additional such projectors with a different stripe distance to be used in order to eliminate ambiguity between various stripes. This ambiguity originates from the fact that the strip pattern is sinusoidal; dark and light strips repeat periodically. These projectors may also each project one single pattern and are activated one after the other. If the stripe period is greater than n adjacent lines, n lines may also be read at a respective distance by more than one pixel. A further advantage of the method according to the invention lies in the fact that there is an extremely short period of time between image acquisitions in various phase positions, and interference with measurement due to vibrations may be suppressed. Thus, by virtue of the fact that the image acquisition duration is very brief, the vibration of the arrangement does not have a negative effect on the image acquisition; therefore, vibration stabilization of the measurement structure is not necessary.

Figure 13A:
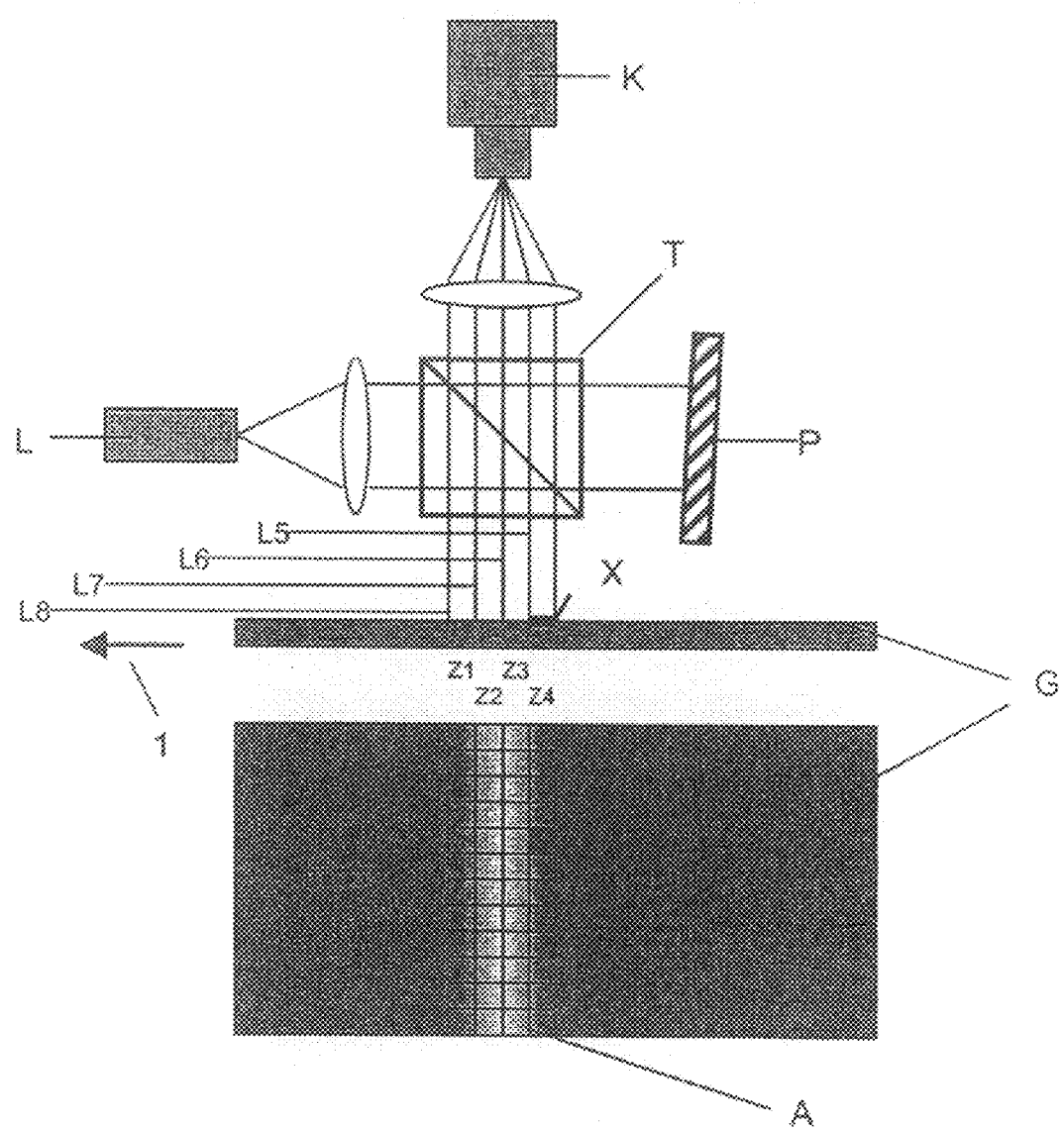
FIG. 13a shows the method according to the invention applied to the interferometric testing method, which is known per se, and is particularly suitable for optically smooth surfaces because it is possible to detect very fine structures whose roughness is less than the wavelength of visible light, i.e., less than approximately 0.5 µm.

In the upper portion of FIG. 13a, a temporally coherent light source, for example, a laser L, may be seen, which serves as the light source. The field of view of a camera K is directed at the test specimen G. Regions L5 to L8 represent the acquisition regions of lines Z1 to Z4 of the camera chip C. A mark X is located in the region of line Z4. The test specimen is moving in the direction of the arrow 1. The beam emitting from the laser L with a certain wavelength is deflected on one side by a beam splitter T onto the surface of the test specimen G and on the other side onto a mirror P. On the surface of the test specimen G, the beam is reflected and returns to the beam splitter T. The beam striking the mirror P is also reflected back to the beam splitter T. In the beam splitter T, the two beams meet again and overlap. The camera K is structured in such a way that the overlapping light strikes it. By virtue of the different lengths of the paths that the light travels to the test specimen G and the fixed mirror P, a difference between the light paths of 0, 1, 2, 3, 4, . . . times the wavelength of the laser, with the overlay (interference) in the beam splitter T, the brightness (constructive interference) results, and in the case of a difference of 0.5, 1.5, 2.5, . . . times the wavelength of the laser, the darkness (destructive interference) results. From the distribution of brightness and darkness (interference stripes), the 3-D shape of the test specimen G may be suggested.

In the lower portion of FIG. 13a, a top view of the test specimen G as well as projections of lines Z1 to Z4 of the camera chip C and the interference pattern created thereby may be seen. The mark X on the surface of the test specimen may also be seen; here, it is located in the region of line Z1.

As described above, a Michelson interferometer is shown by way of example as the interferometer type; however, other types such as Mach-Zehnder and many others are possible as well. Although the mechanism of producing the interference stripes is completely difference from that of stripe projection, the method according to the invention may be transferred from stripe projection to interferometry in a virtually 1:1 fashion. Here as well, by suitably selecting the stripe periods (for example, by tilting the mirror P or the plane of the test specimen G) to fit the distance of n lines, it is possible to be able to capture phase-shifted intensity values in the n lines; for n=4, 0° in line Z4, 90° in Z3, 180° in Z2, and 270° in Z1. Here as well, a significant simplification and reduction in costs results because a static interferometer may be used without a device for phase shifting. In this case, the temporal succession of the n illuminations is replaced by the spatial progression of n illuminations. Each phase position of the illumination, for example, 0°, 90°, 180°, 270°, which occur one next to the other spatially, corresponds to an illumination Bn. Sensitivity to vibrations of the measuring apparatus and/or the interferometer is also significantly reduced. By virtue of the fact that the image acquisition occurs so quickly, vibrations that are caused by environmental influences do not have any negative effects on image acquisition.

Alternately, different stripe distances may be realized, for example, by one or more additional light sources with different wavelengths (multiple-wavelength interferometry). These light sources may be connected with a short time difference from one another, in particular when they are semiconductor lasers.

Figure 13B:
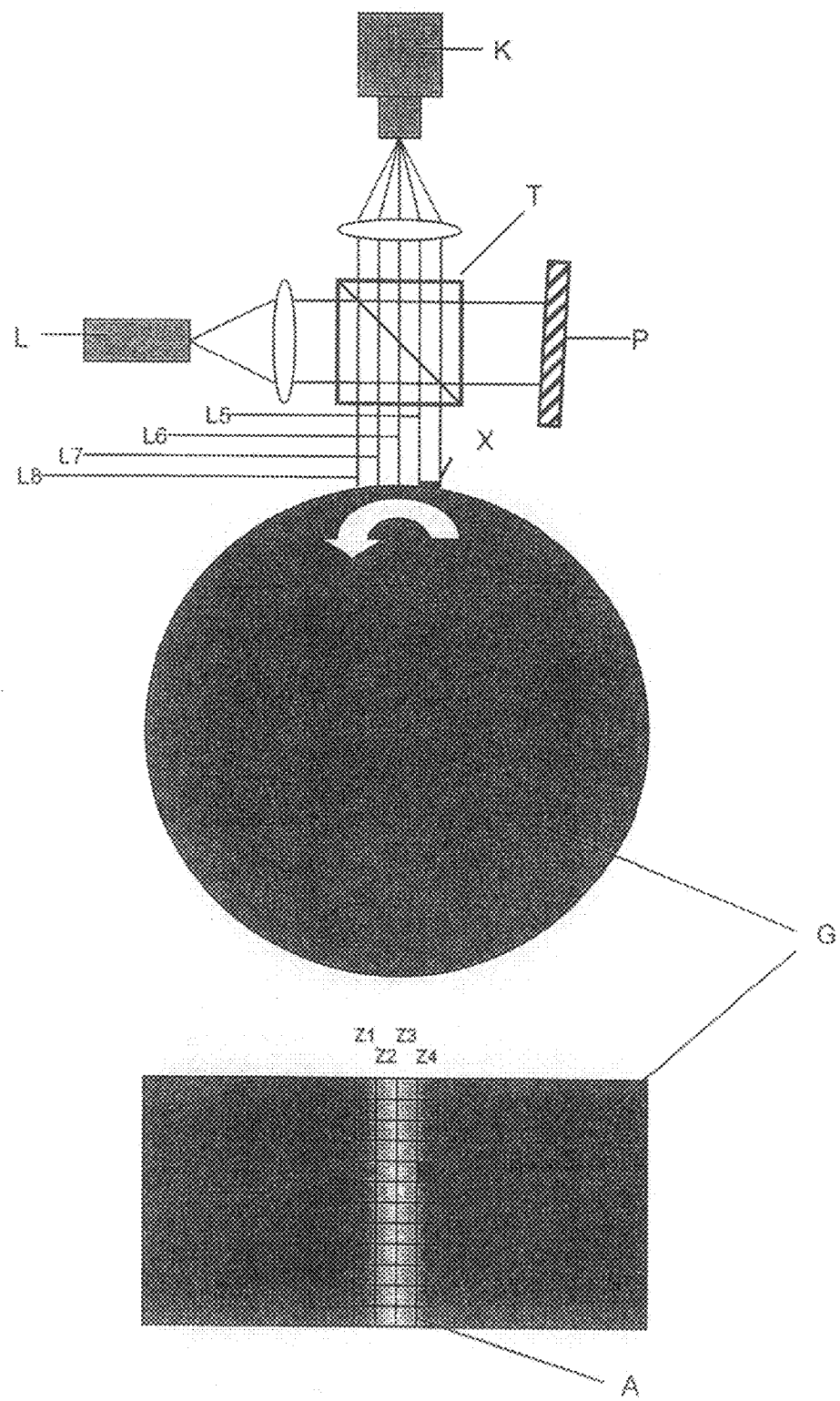

FIG. 13b shows an application for rotational movement of a test specimen G in the direction of the arrow 1 around a rotational axis 3 and for the capture of essentially rotationally symmetrical test specimens G which up to now were accessible for interferometric testing not at all or only with difficulty. The same parts are designated using the same reference characters; in this regard, we refer to the preceding figures.

Figure 14A:
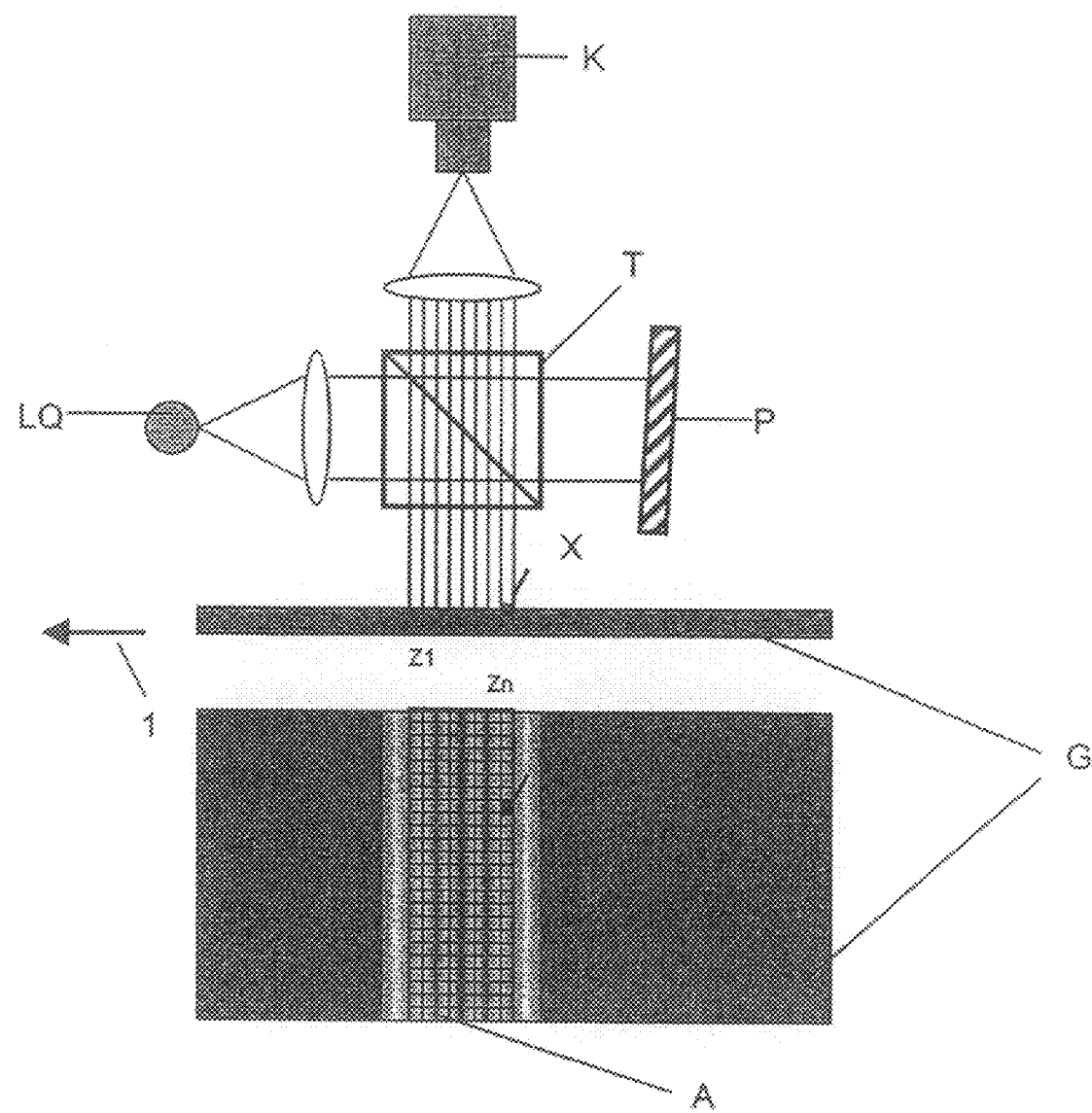

FIG. 14a shows the method according to the invention for the method of white light interferometry, which is known per se and which is suitable for optically smooth surfaces as well as for optically rough ones, i.e., surfaces whose roughness is greater than approximately 0.5 μm.

In the upper portion of FIG. 14, a light source LQ, a camera K, a beam splitter T, and a mirror P are shown. The field of view of the camera K is directed at the test specimen G, which is moving in the direction of the arrow 1. The light source LQ may, for example, be LEDs, incandescent lamps, or the like. Multiple wavelengths contribute to the incidence of interference. The maximum brightness results when both light paths, i.e., from the beam splitter T to the mirror P and back, and from the beam splitter T to the test specimen G, have the same length. As a rule, it is necessary to displace either the mirror P or the test specimen G in very many small steps (for example, by one quarter of a wavelength each time) in order to equalize the two light paths. Variations in brightness are then captured by the camera K.

In this method, it is advantageous for the stripe periods to be selected in such a way that, for example, four lines Z1 to Z4 correspond to a stripe period; other numbers are possible as well. Because the stripe contrast in white light interferometry increases or decreases from one stripe to the next, it is advisable here to record more than one stripe and, for example, to read 100×4 lines. The maximum for the stripe contrast indicates the height above the plane of movement at which a mark is located. Here as well, advantages of the method according to the invention are that no device is required for phase shifting and the structure may therefore be realized in a simple and cost-effective manner, and influences of vibrations may be suppressed by the rapid image capture.

Figure 14B:
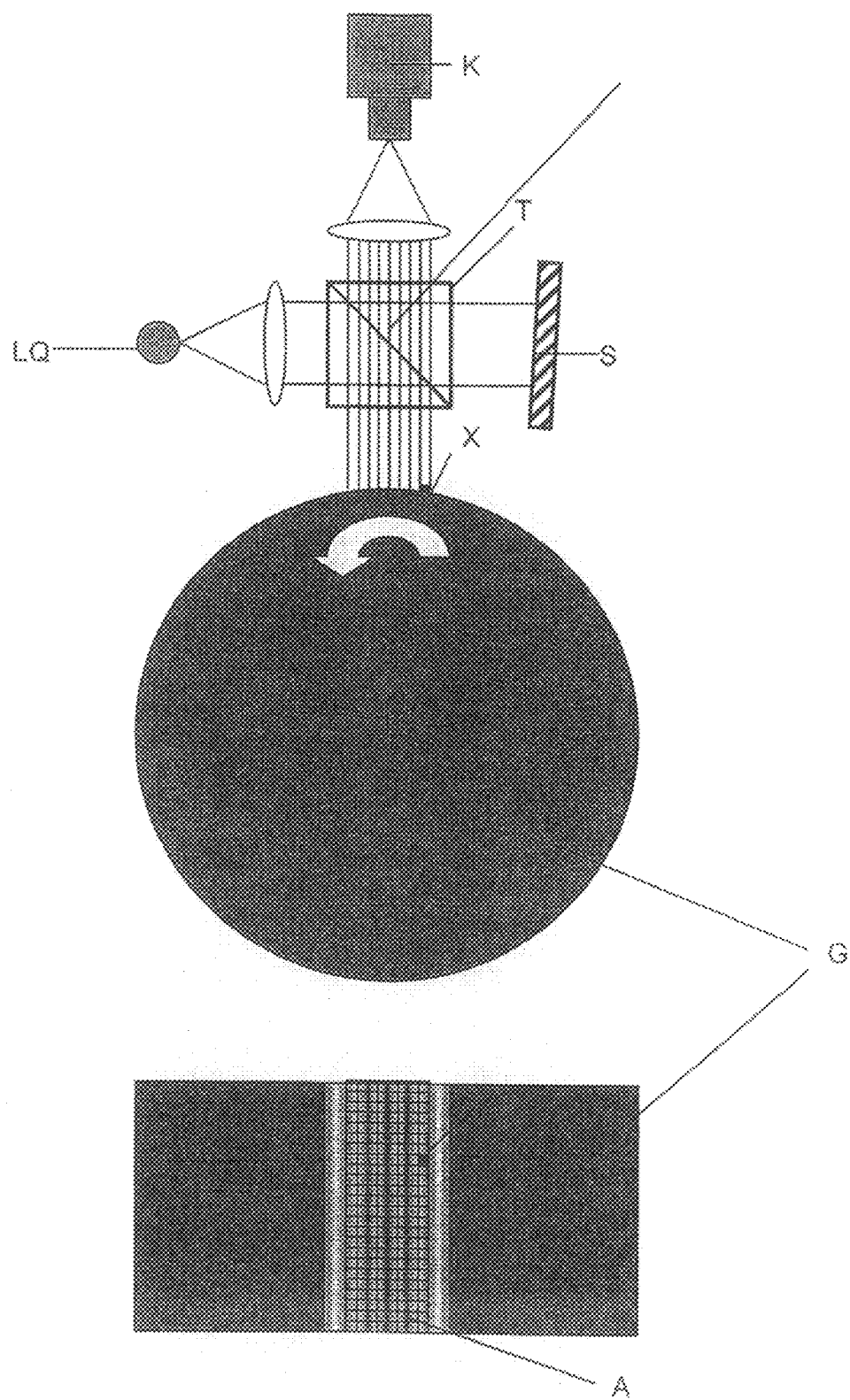

Here as well, the temporal succession of the n illuminations is replaced by the spatial progression of n illuminations. Each phase position of the illumination, which occur one next to the other spatially, corresponds to an illumination Bn. In addition, the white light interferometry is practicable for measuring the coating surface of essentially rotationally symmetrical parts. FIG. 14b shows a structure in a side view and a top view in which a rotationally symmetrical test specimen G rotates in the direction of the arrow 1 around a rotational axis 3.

Alternately, instead of a matrix camera, a special camera K may be used as well whose camera chip C includes only a few lines. Of particular interest are cameras and chips that, for example, include two, three, four up to approximately 100 lines. Such cameras represent the transition between line cameras and matrix cameras.

Figure 1A:
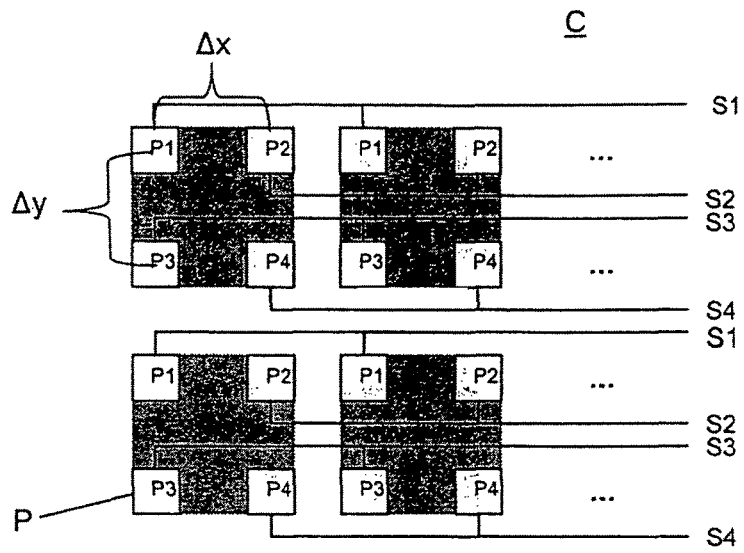
Figure 1B:
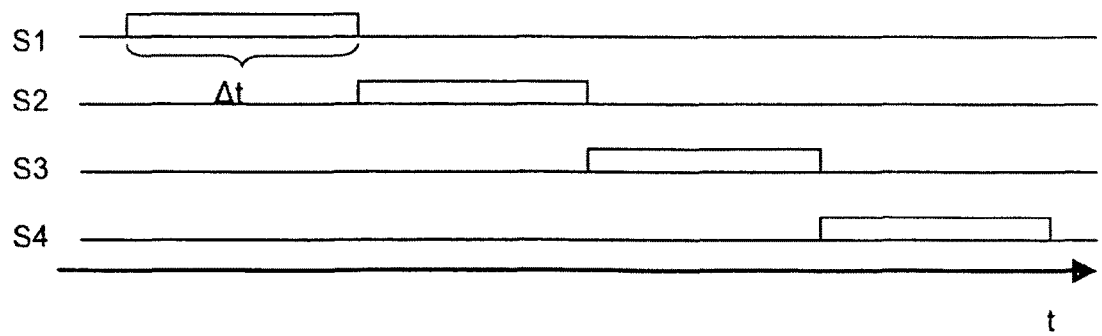
Figure 2A:
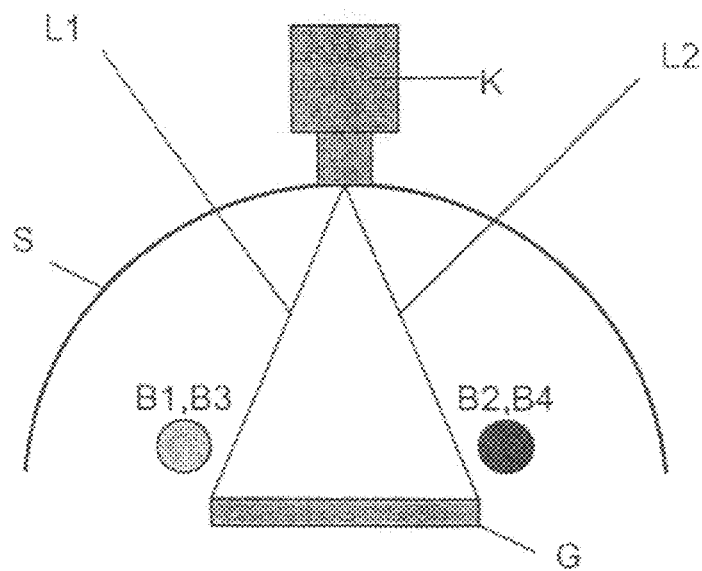
Figure 2A:
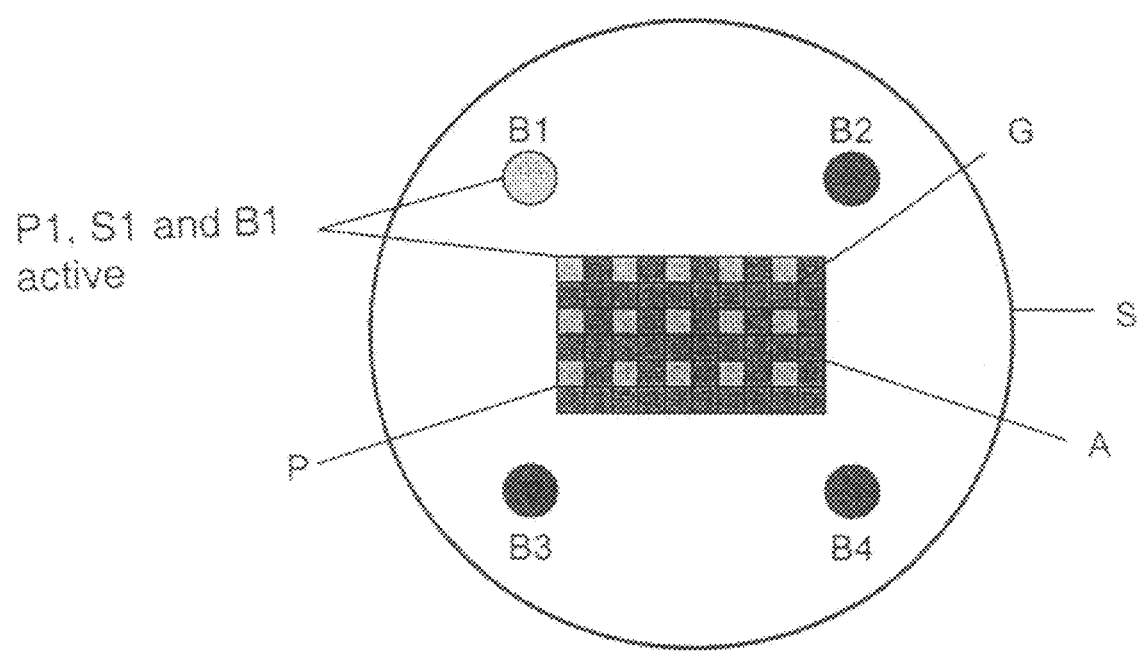
Figure 2B:
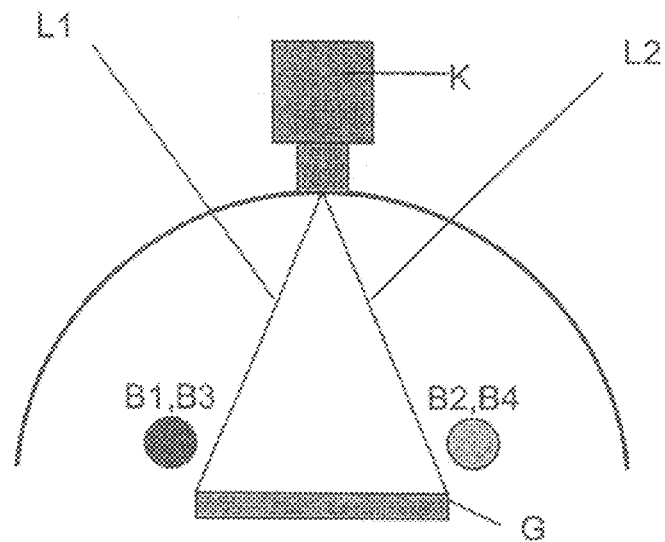
Figure 2B:
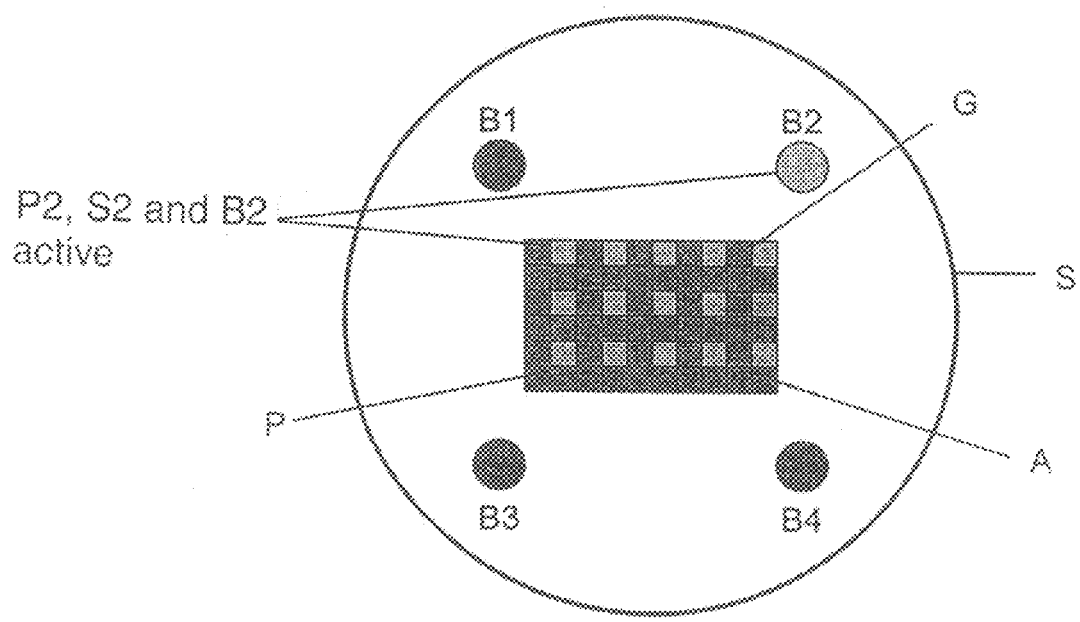
Figure 2C:
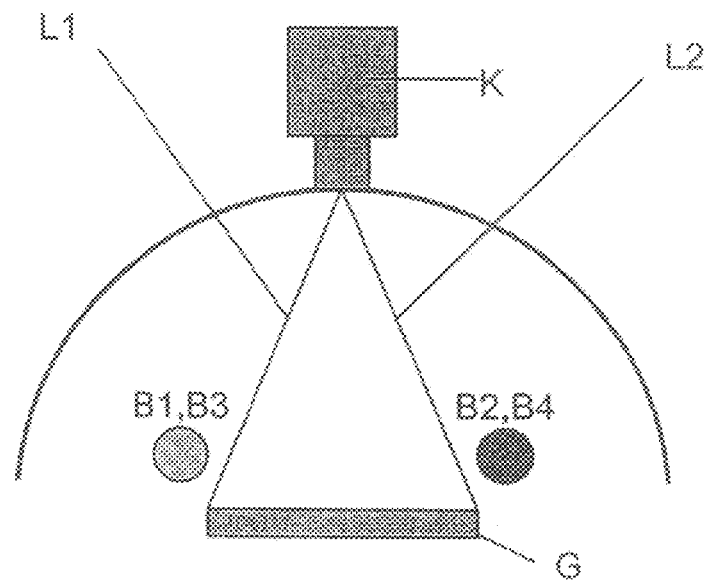
Figure 2C:
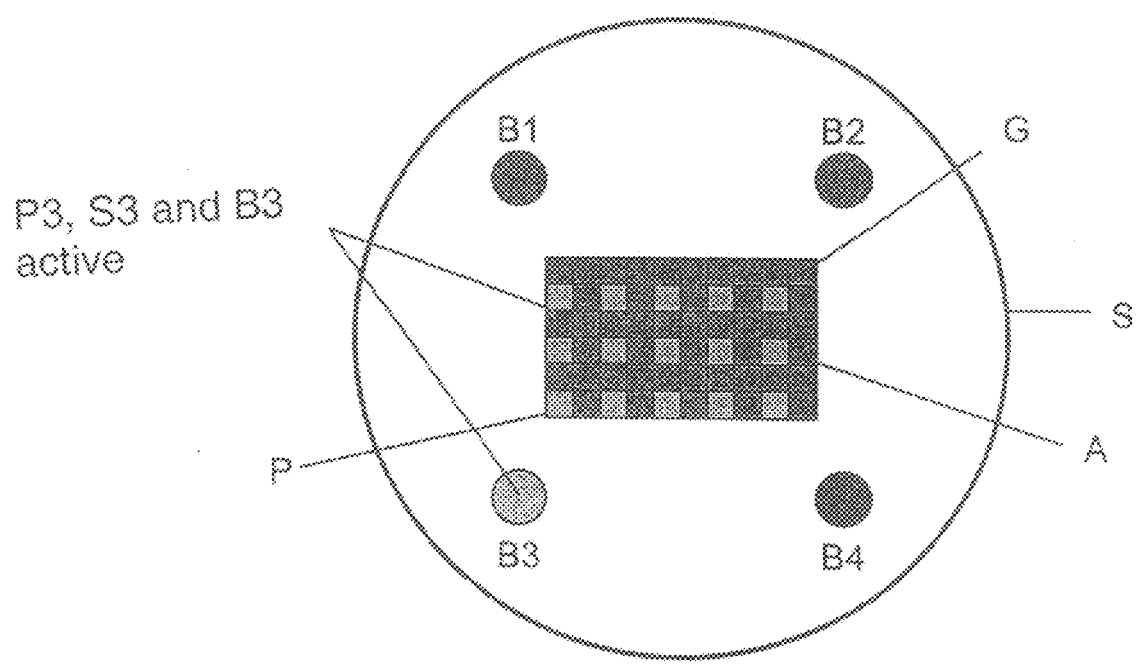
Figure 2D:
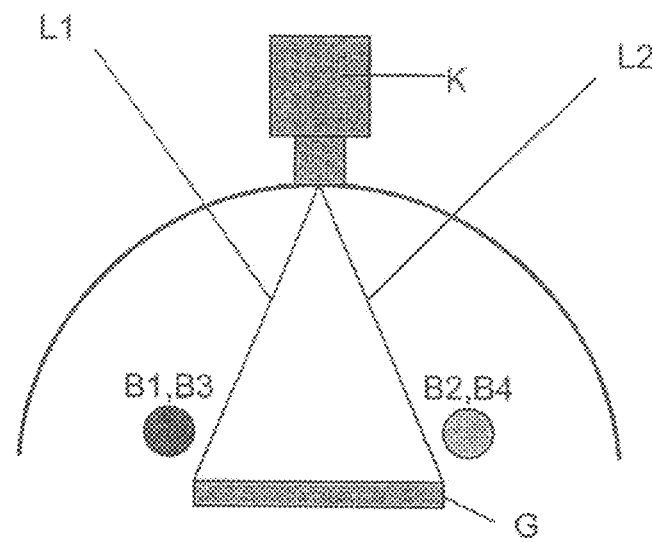
Figure 2D:
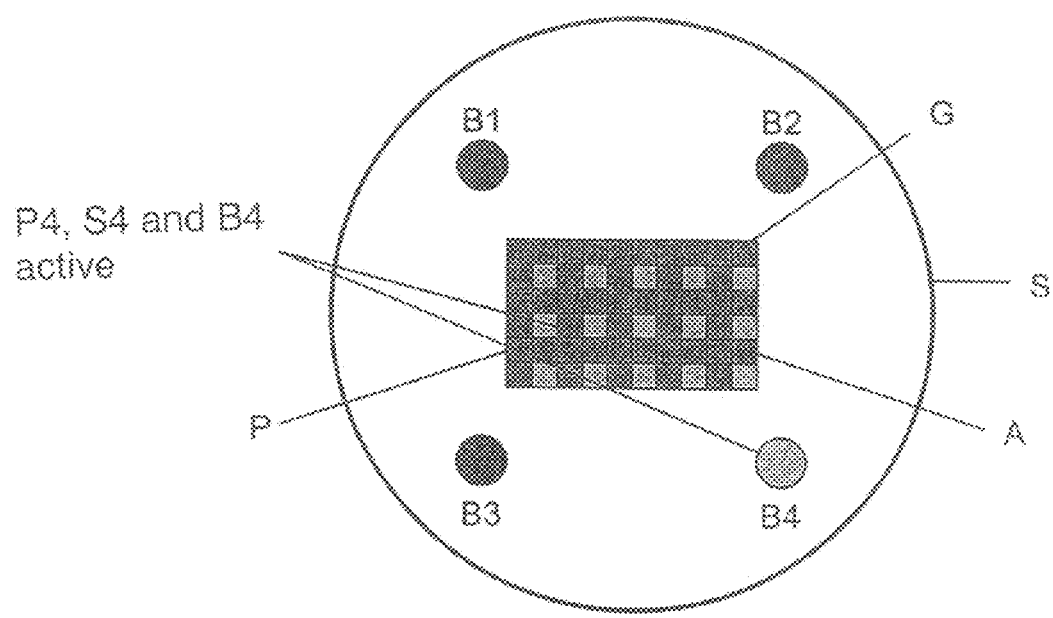
Figure 2E:
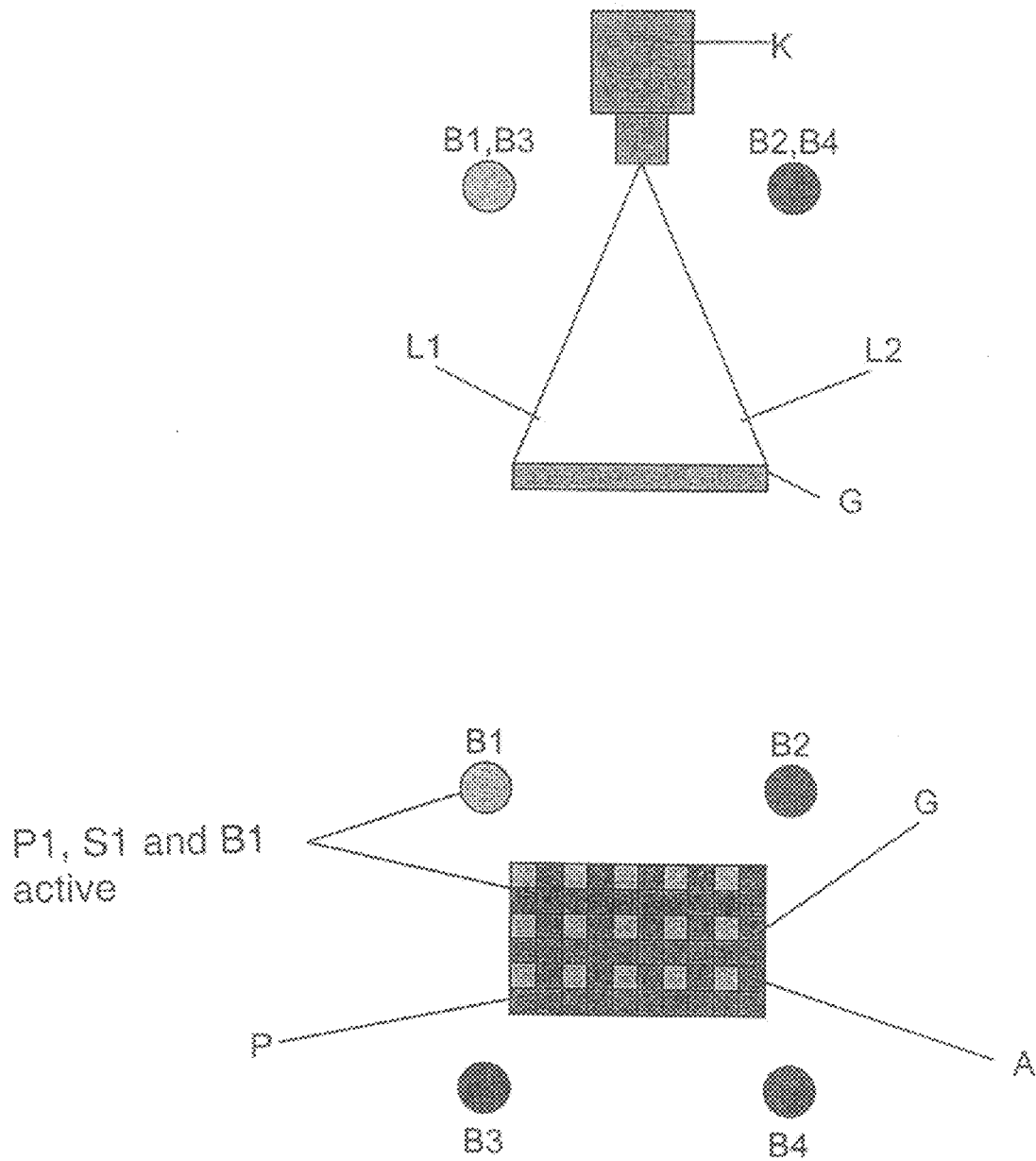
Figure 3A:
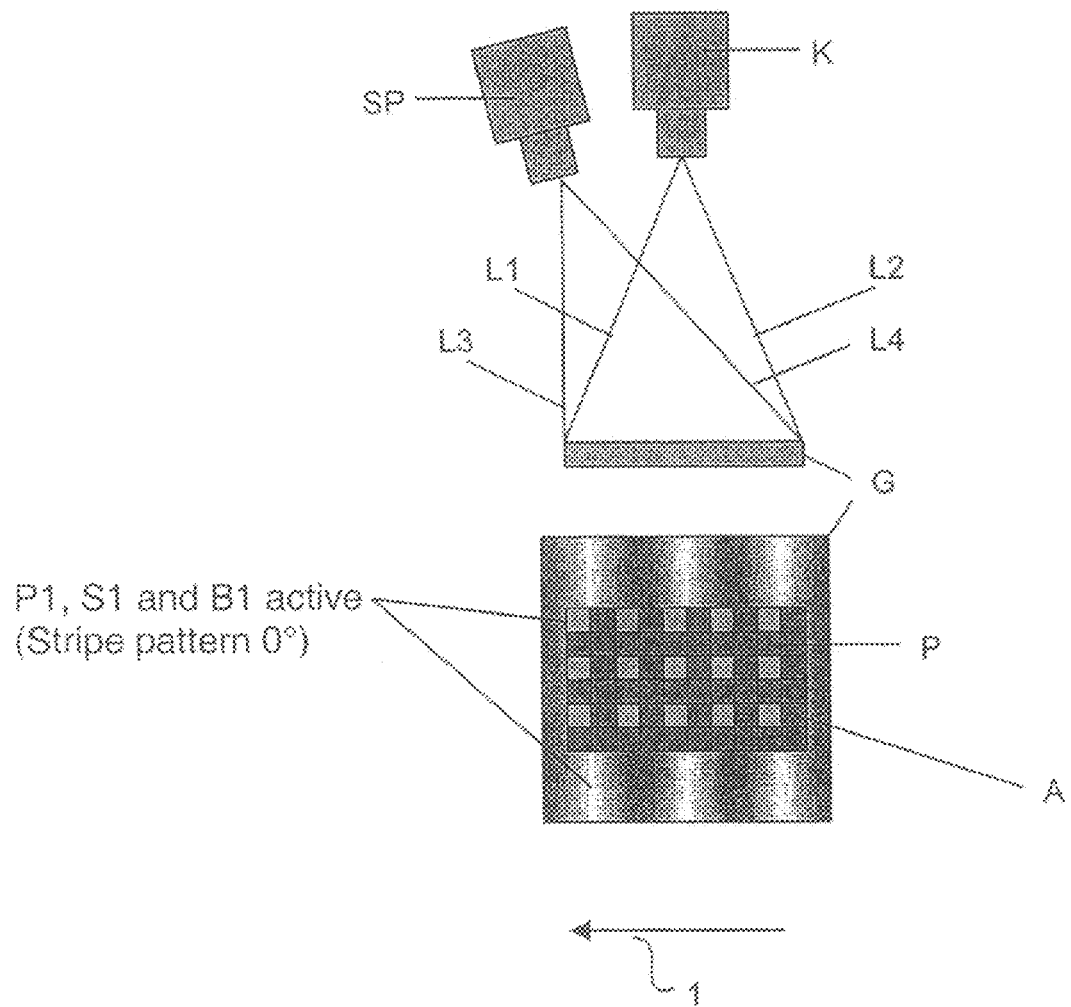
Figure 3B:
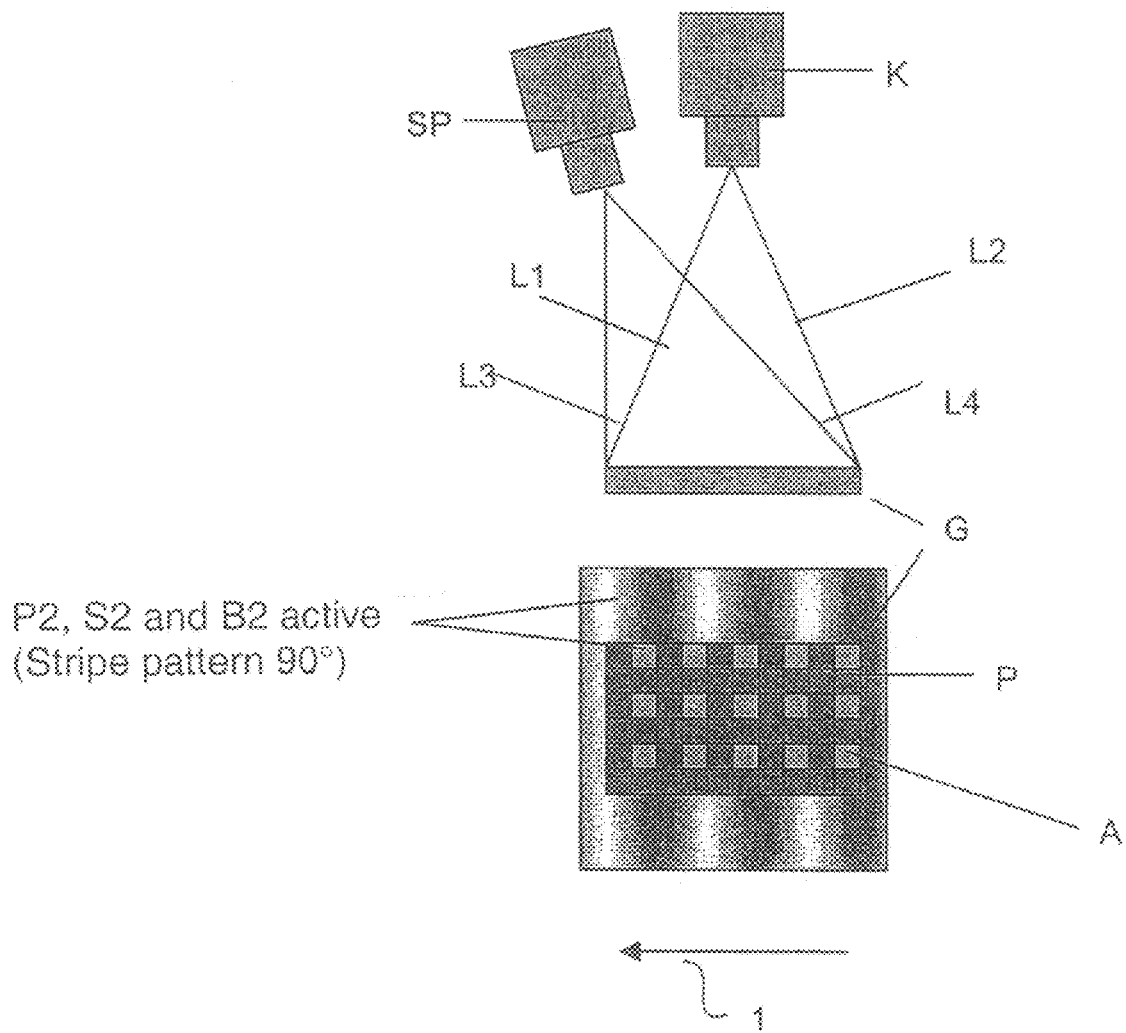
Figure 3C:
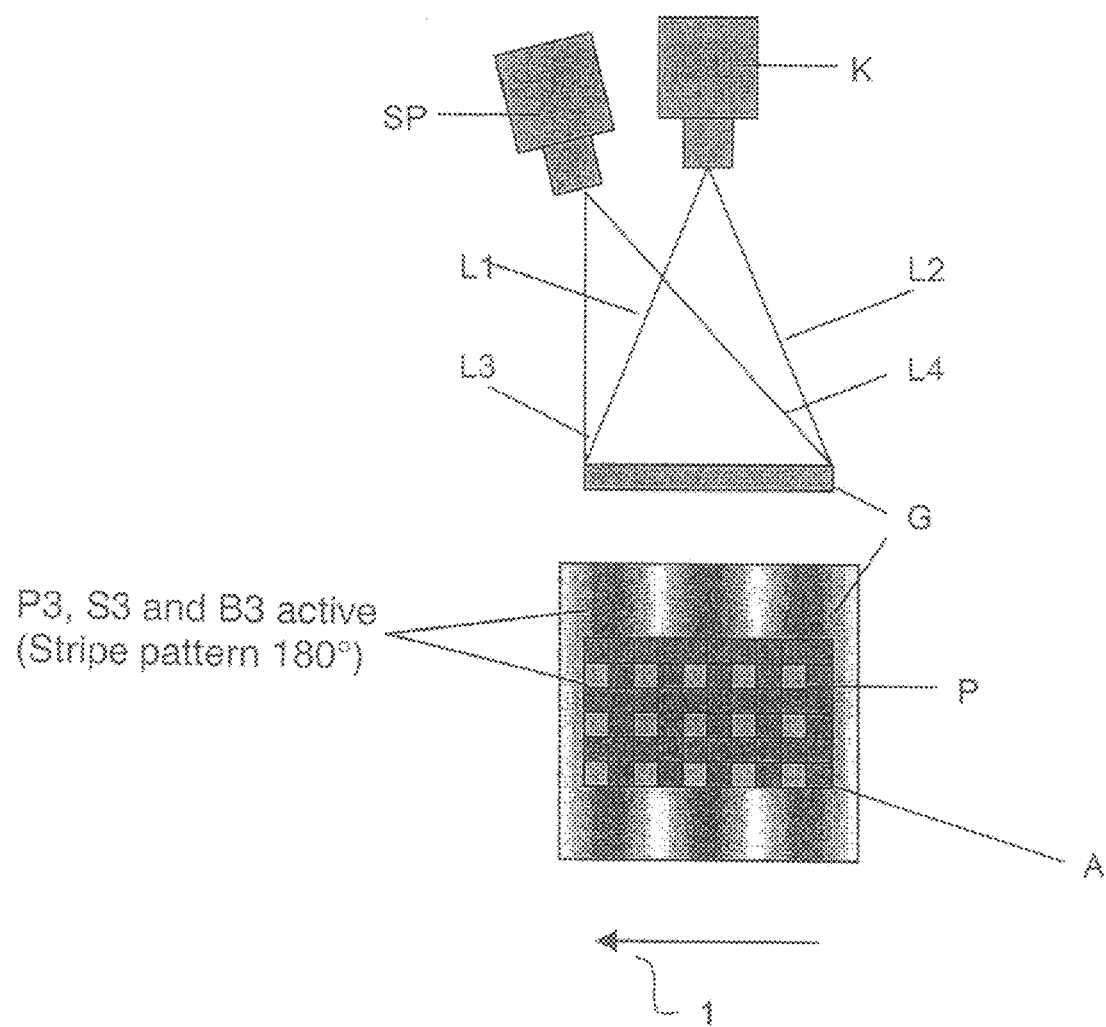
Figure 3D:
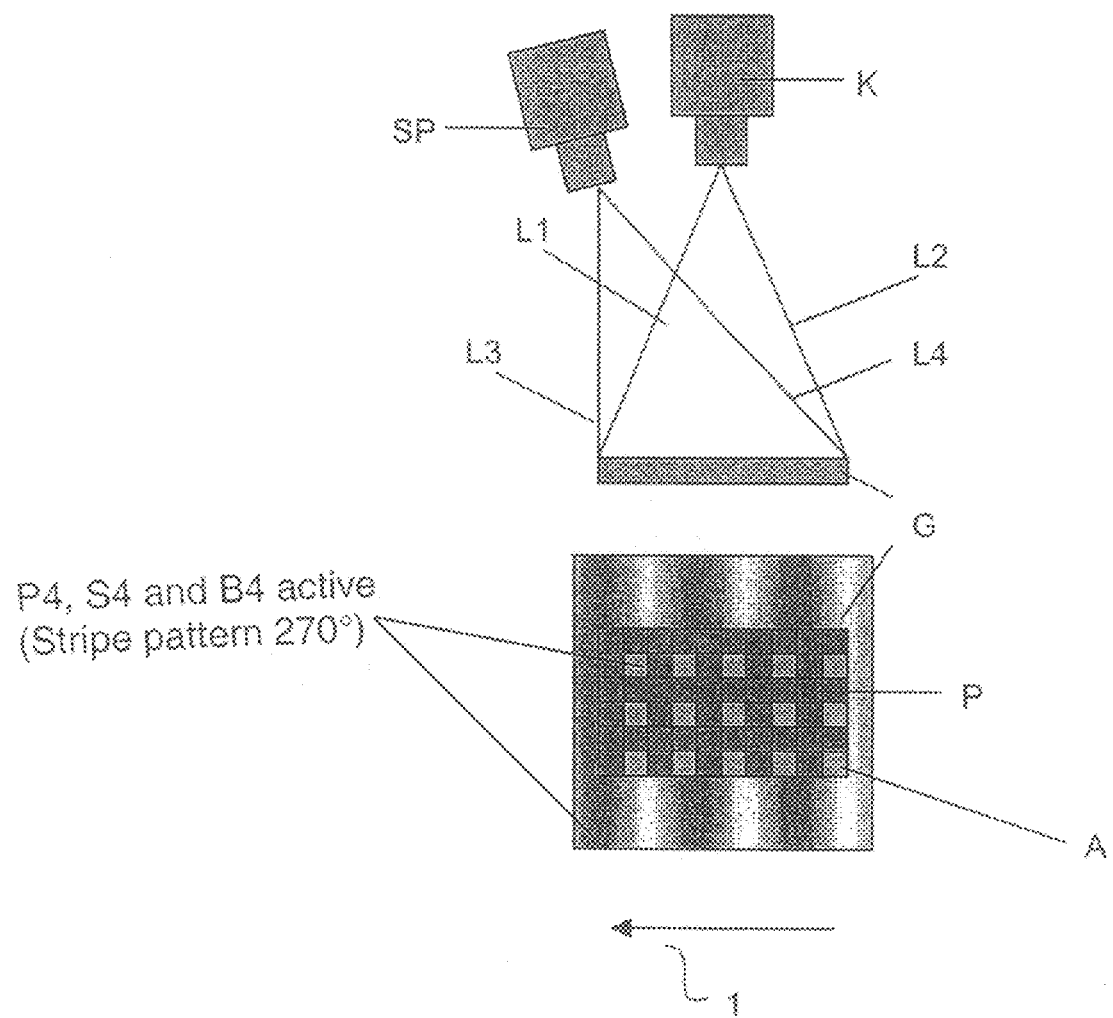
Figure 3E:
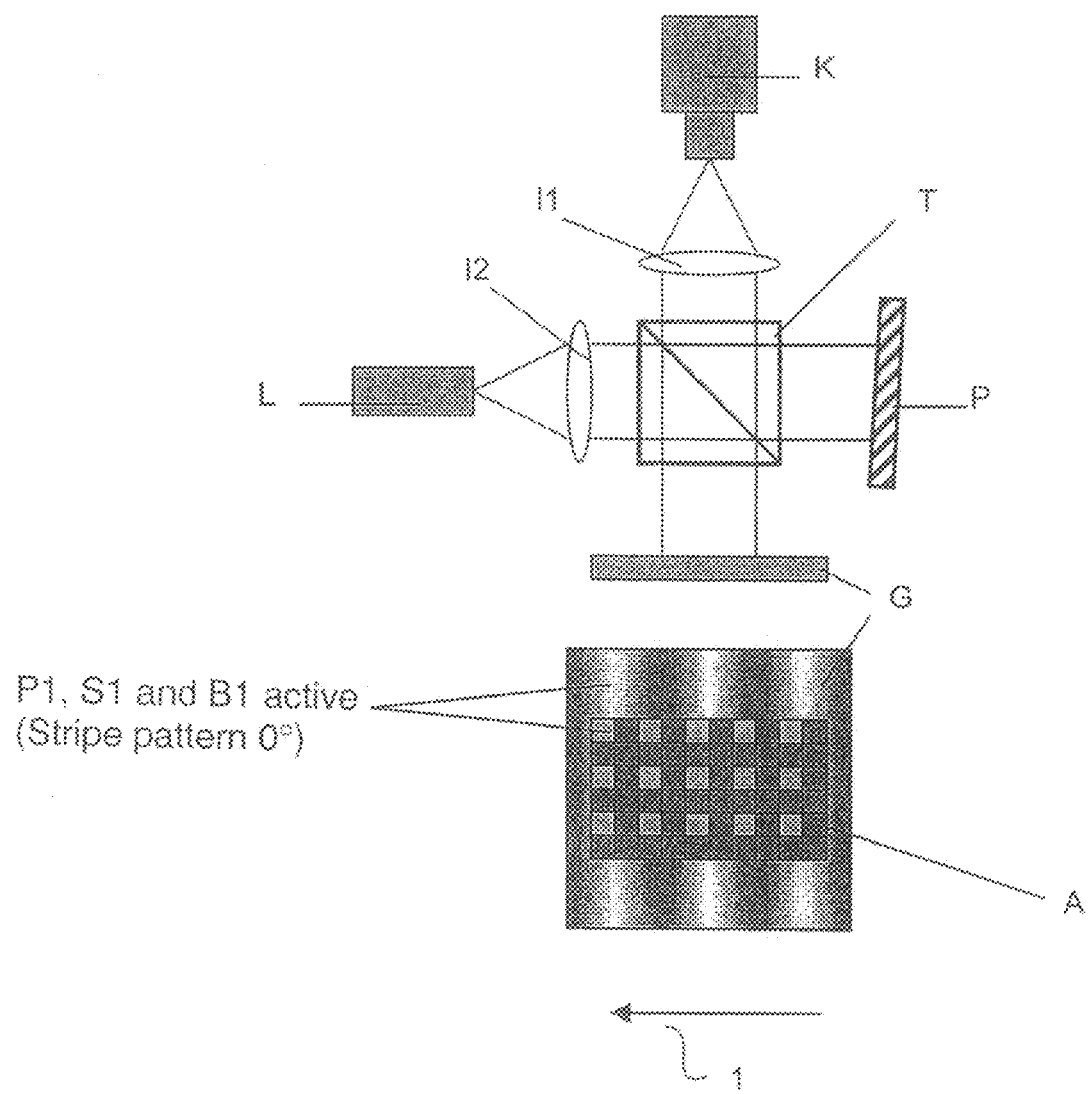
Figure 4A:
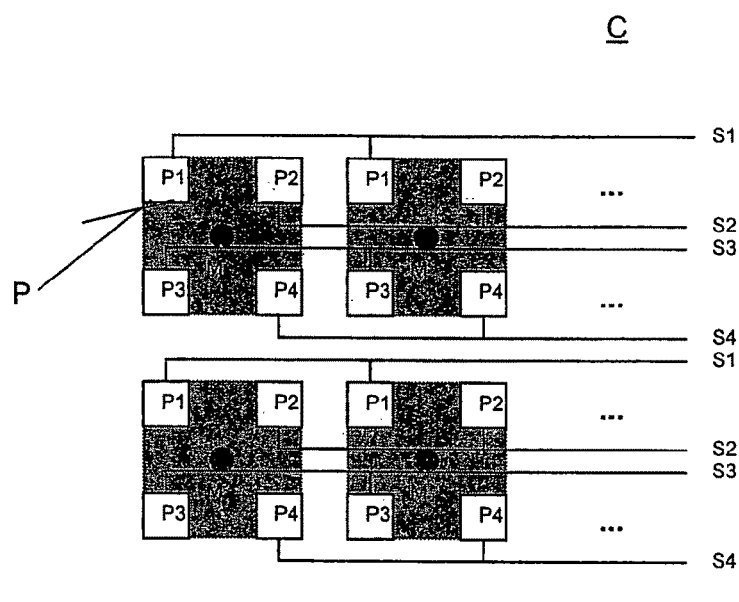
Figure 4B:
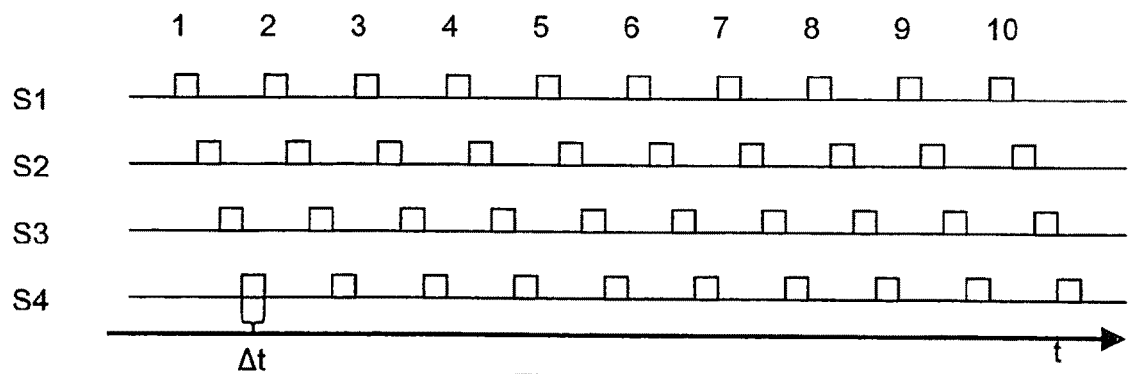
Figure 5:
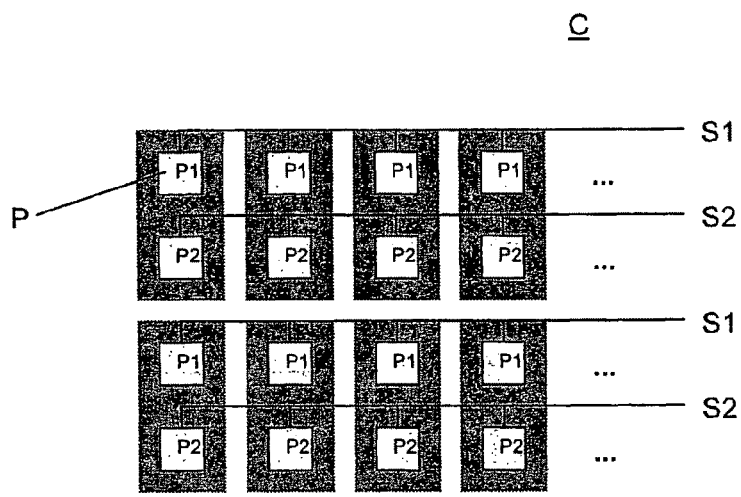
Figure 6:
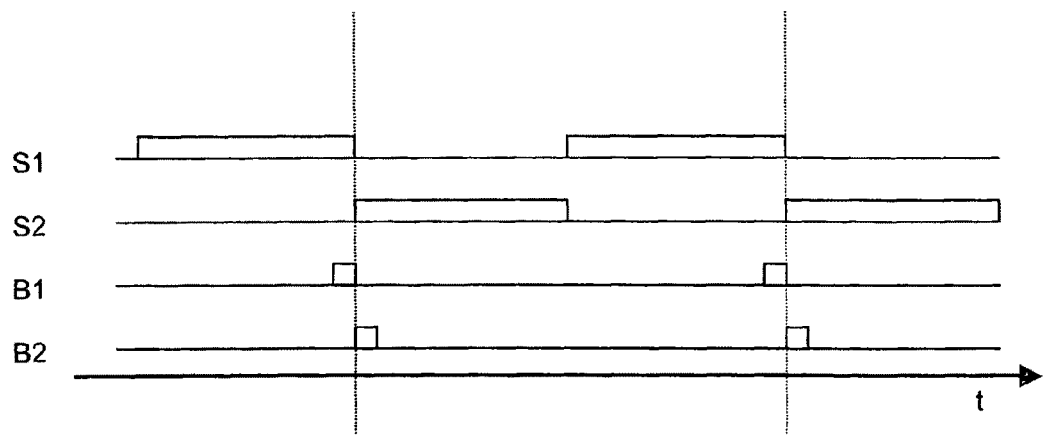
Figure 7:
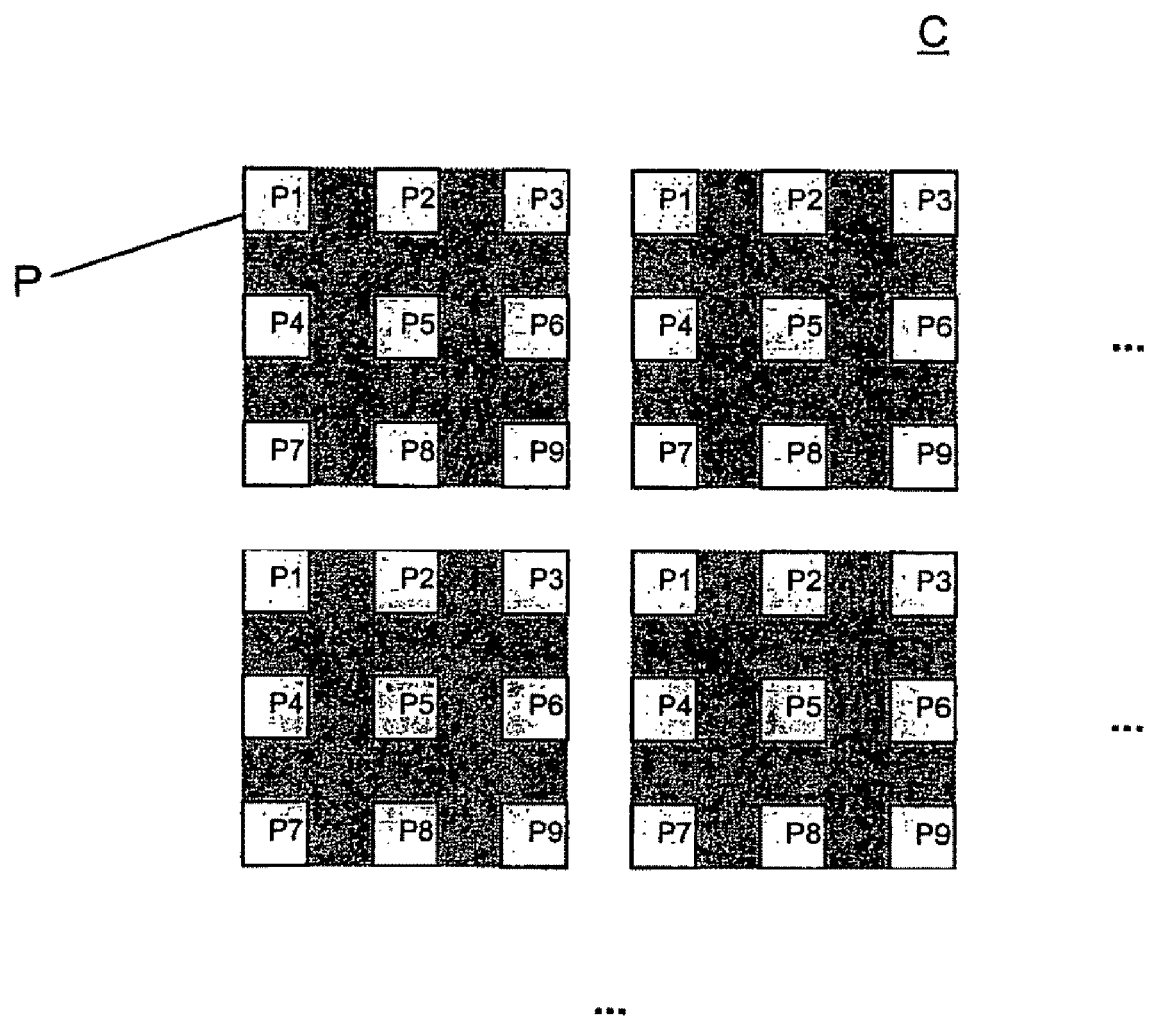
Figure 8A:
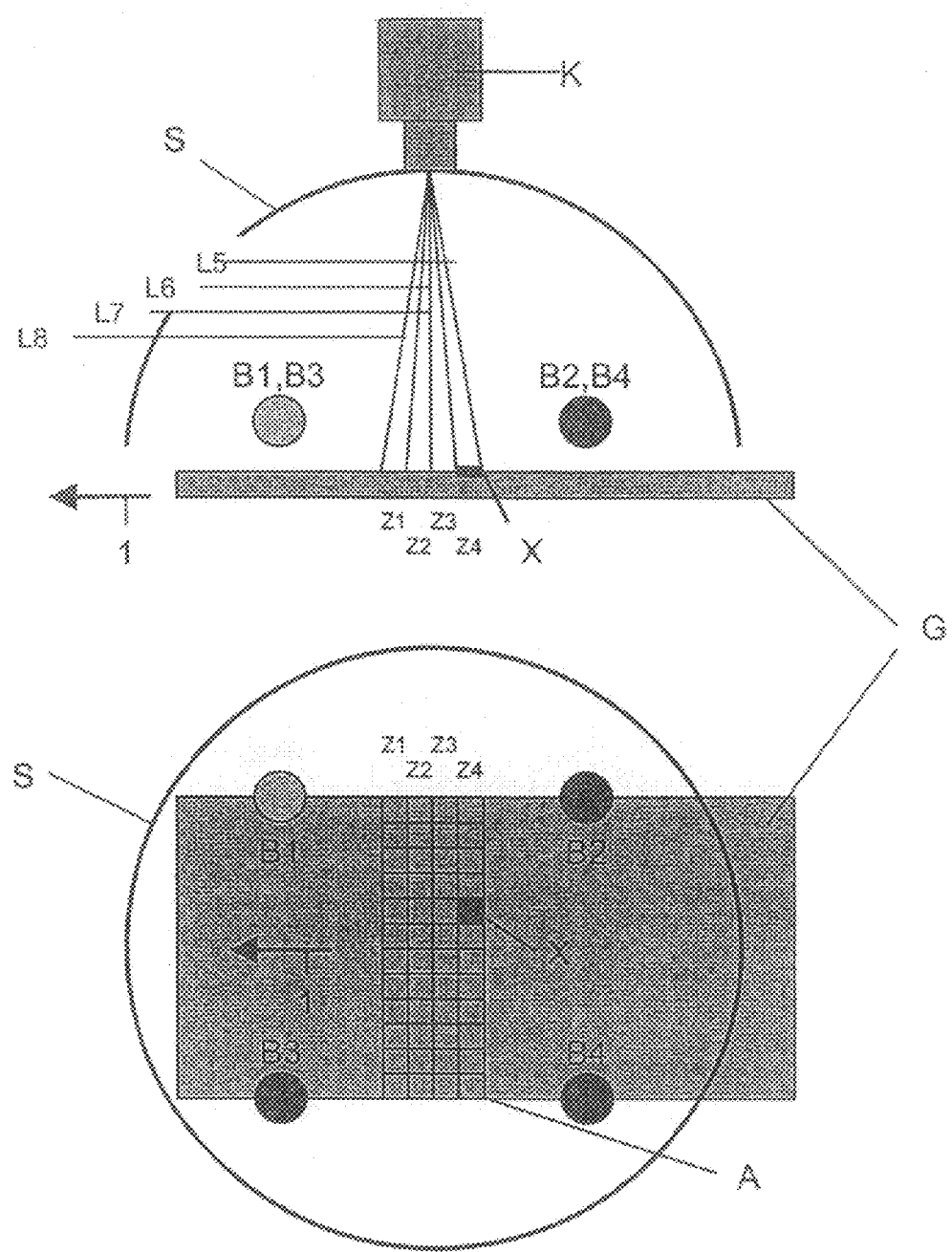
Figure 8B:
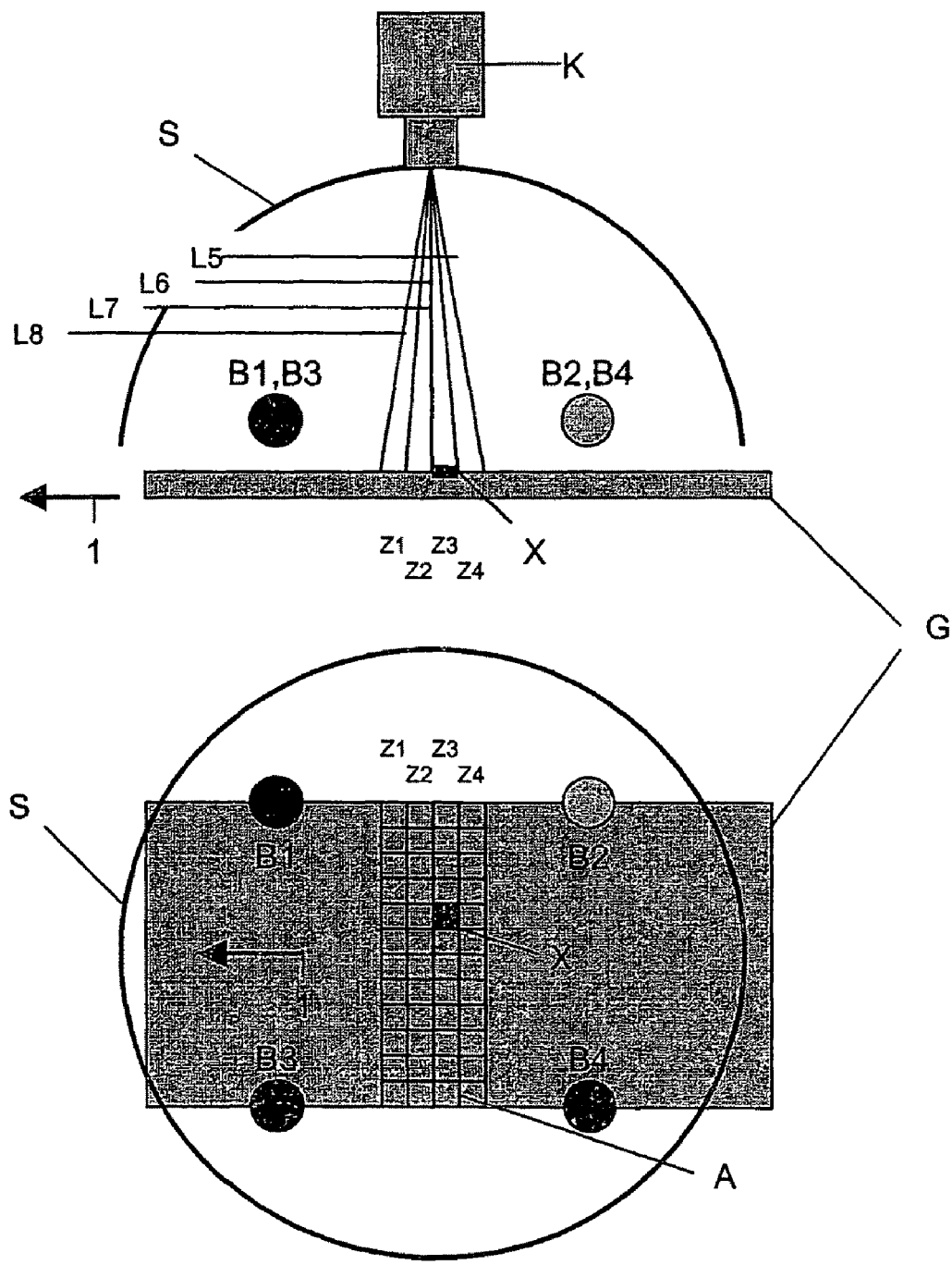
Figure 8C:
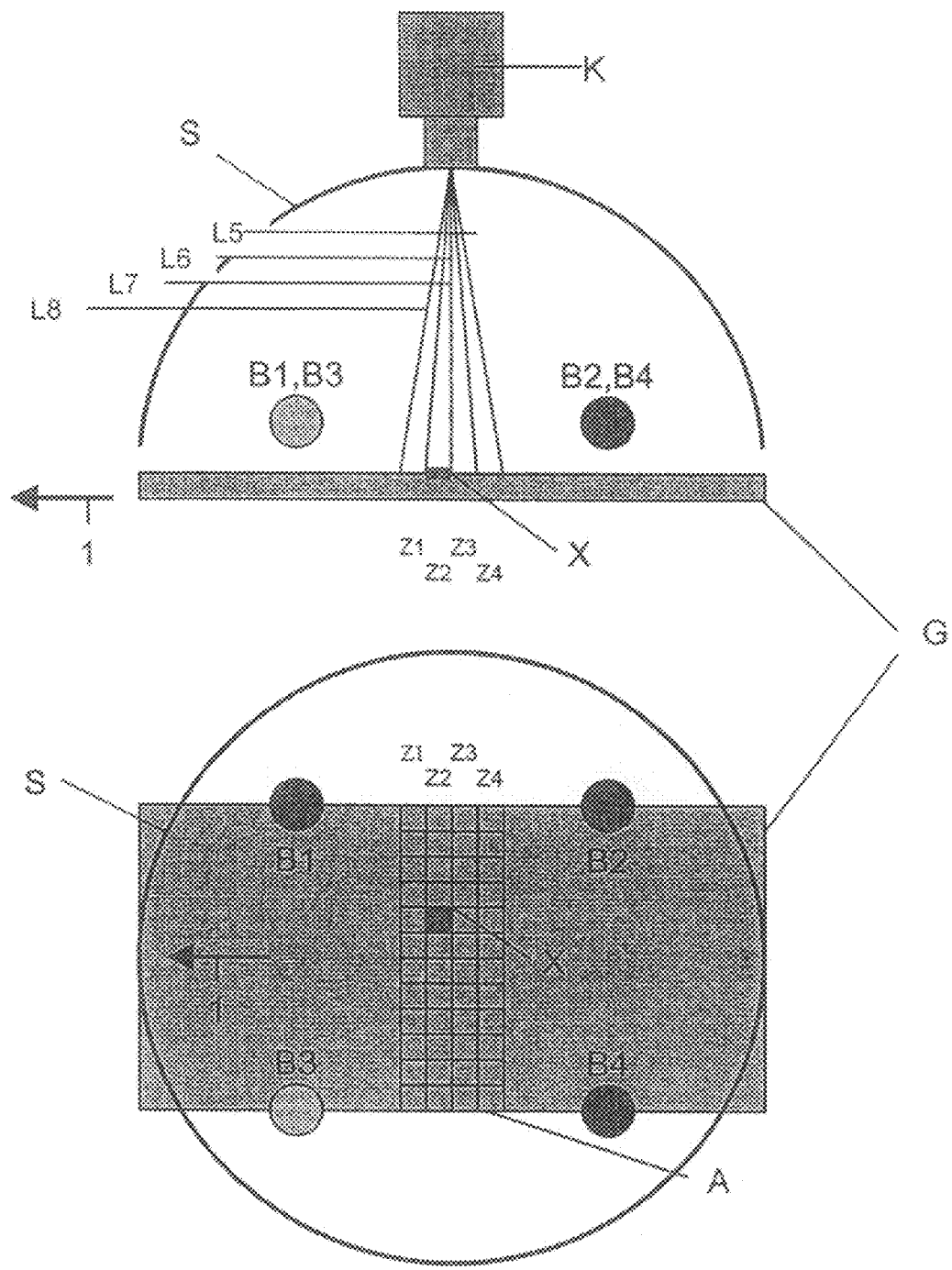
Figure 8D:
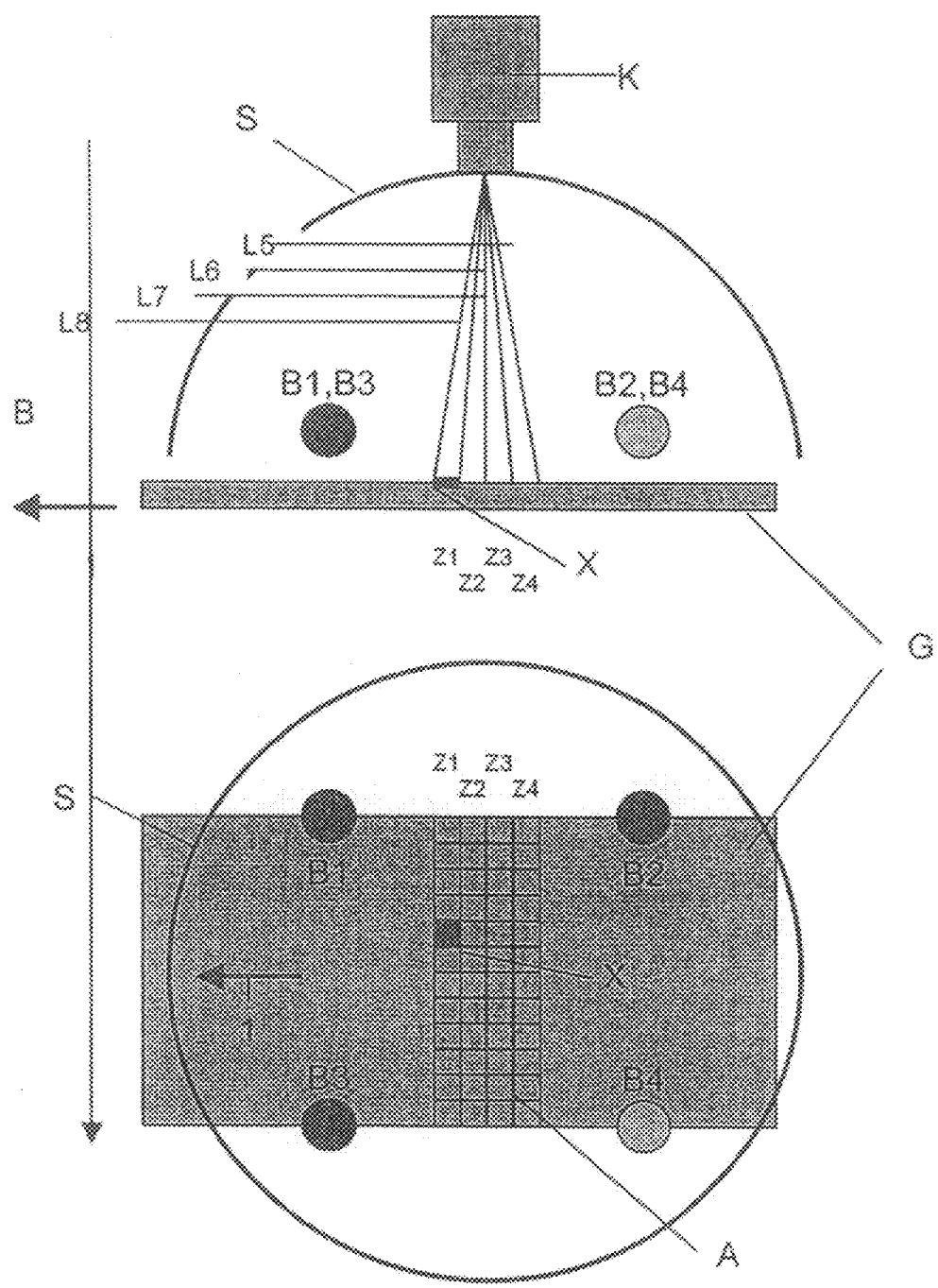
Figure 8E:
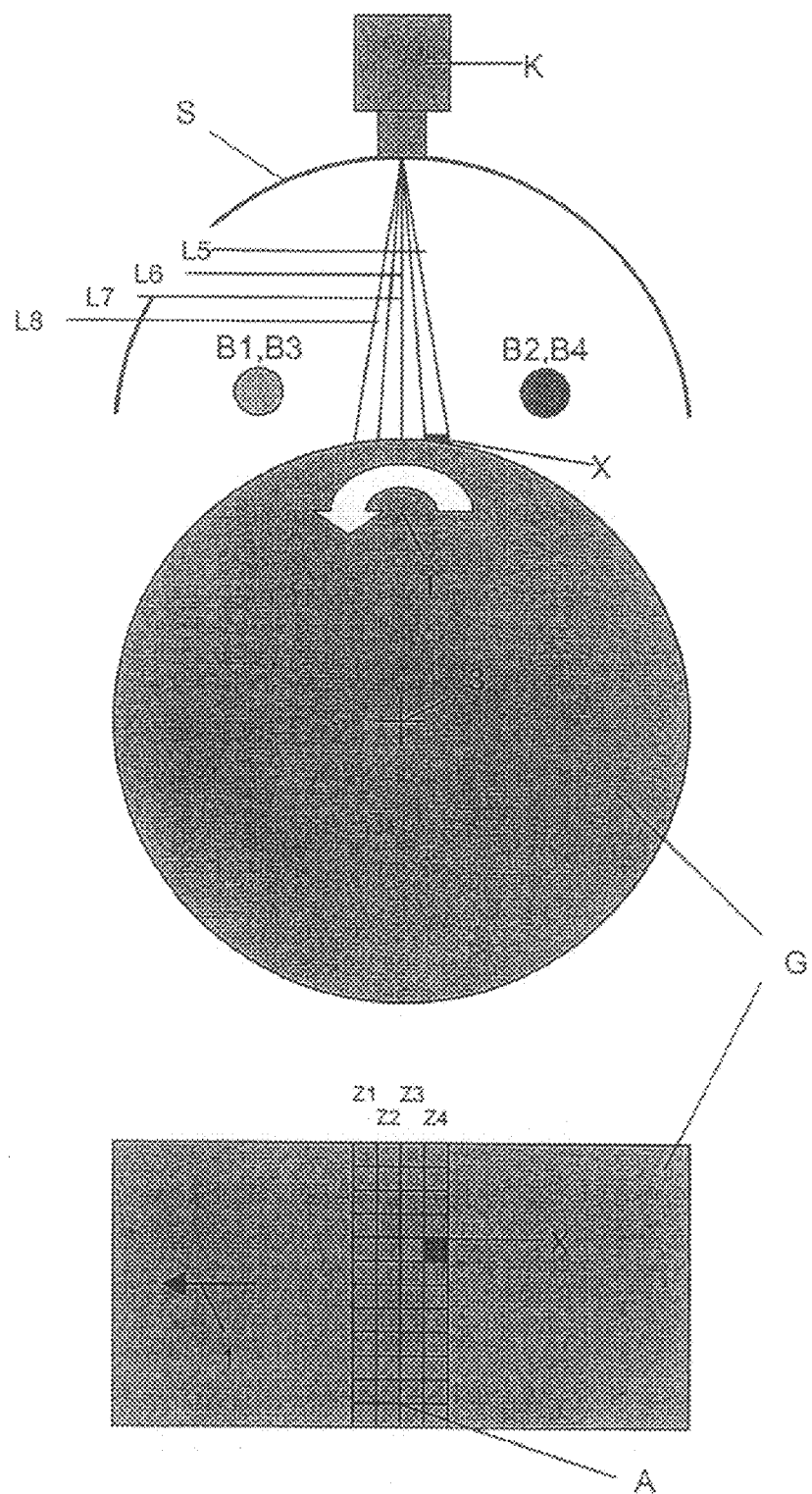
Figure 9A:
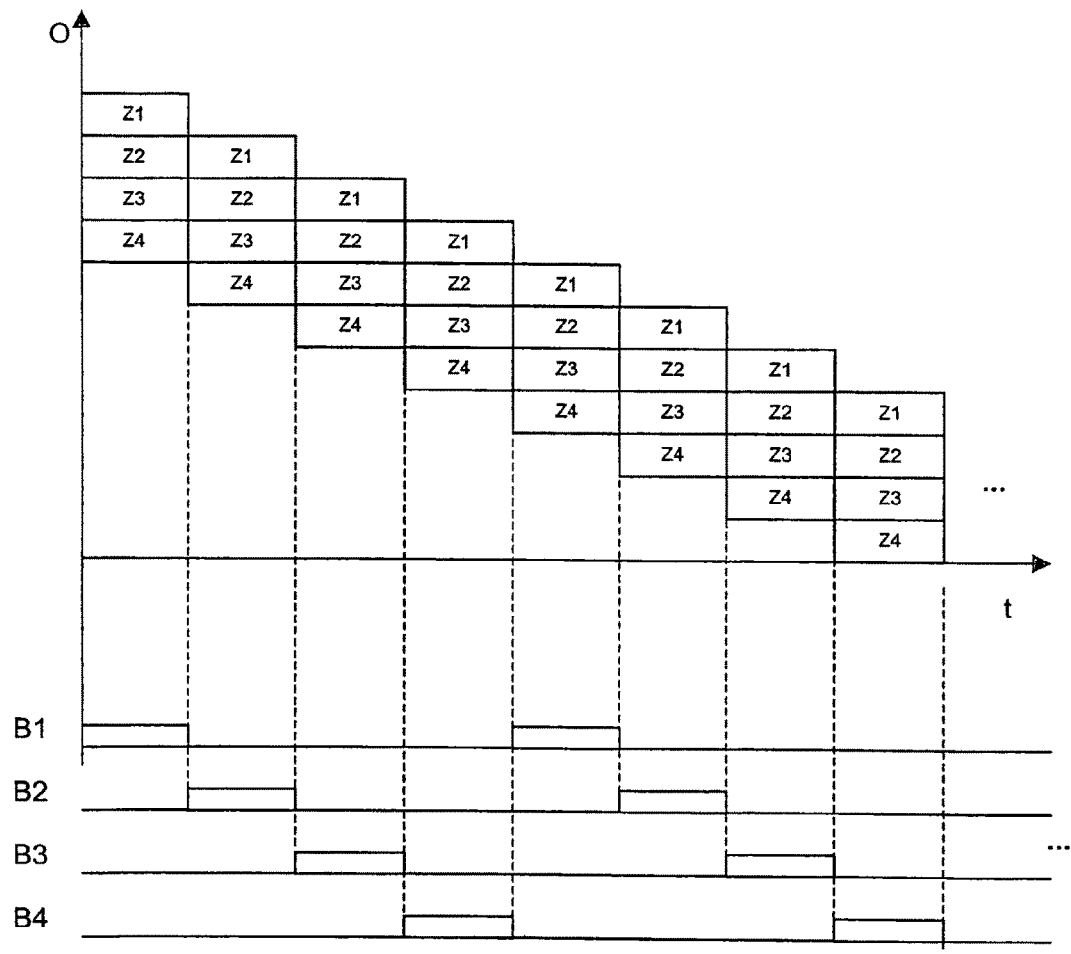
Figure 9B:
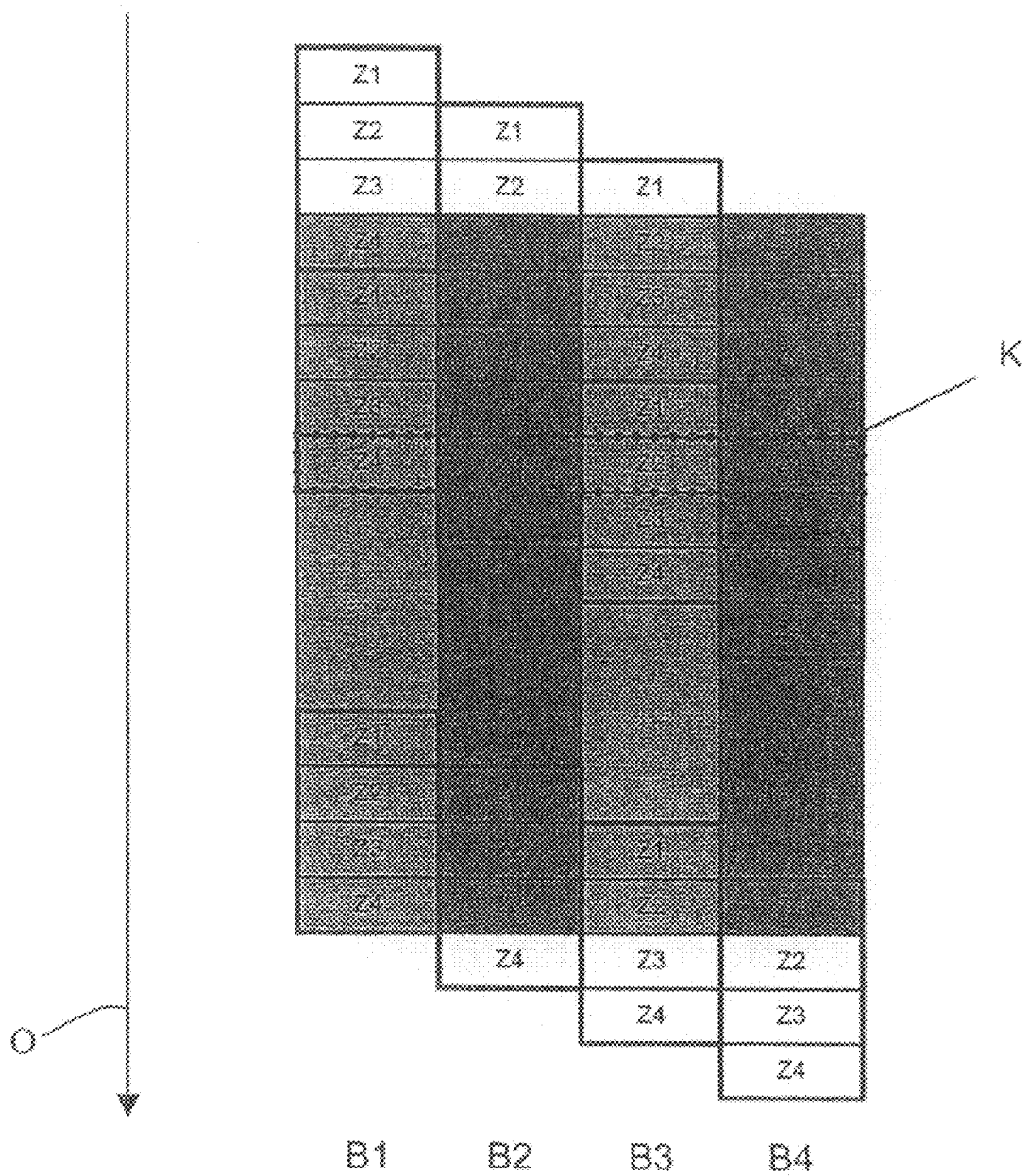
Figure 10A:
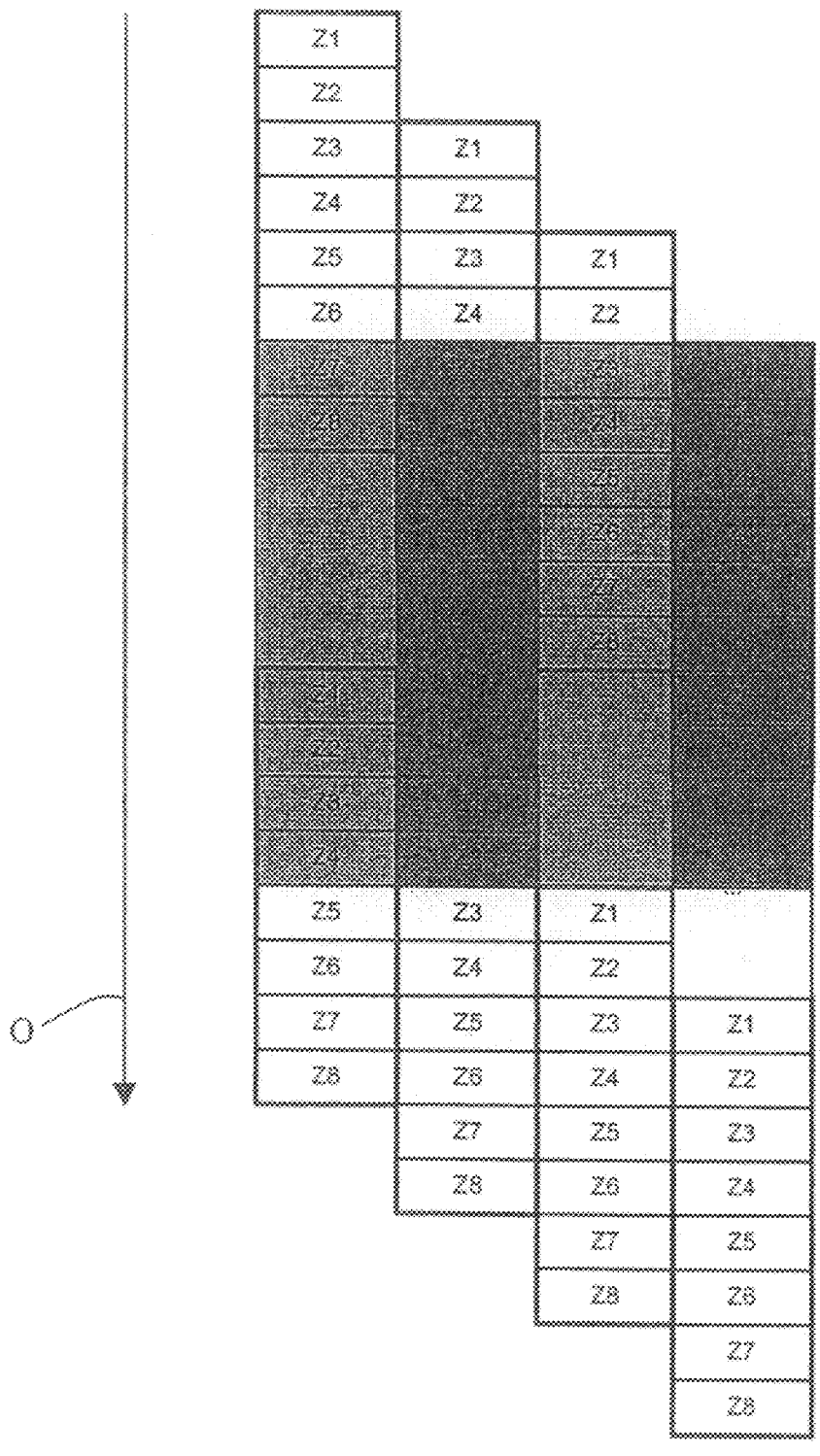
Figure 10B:
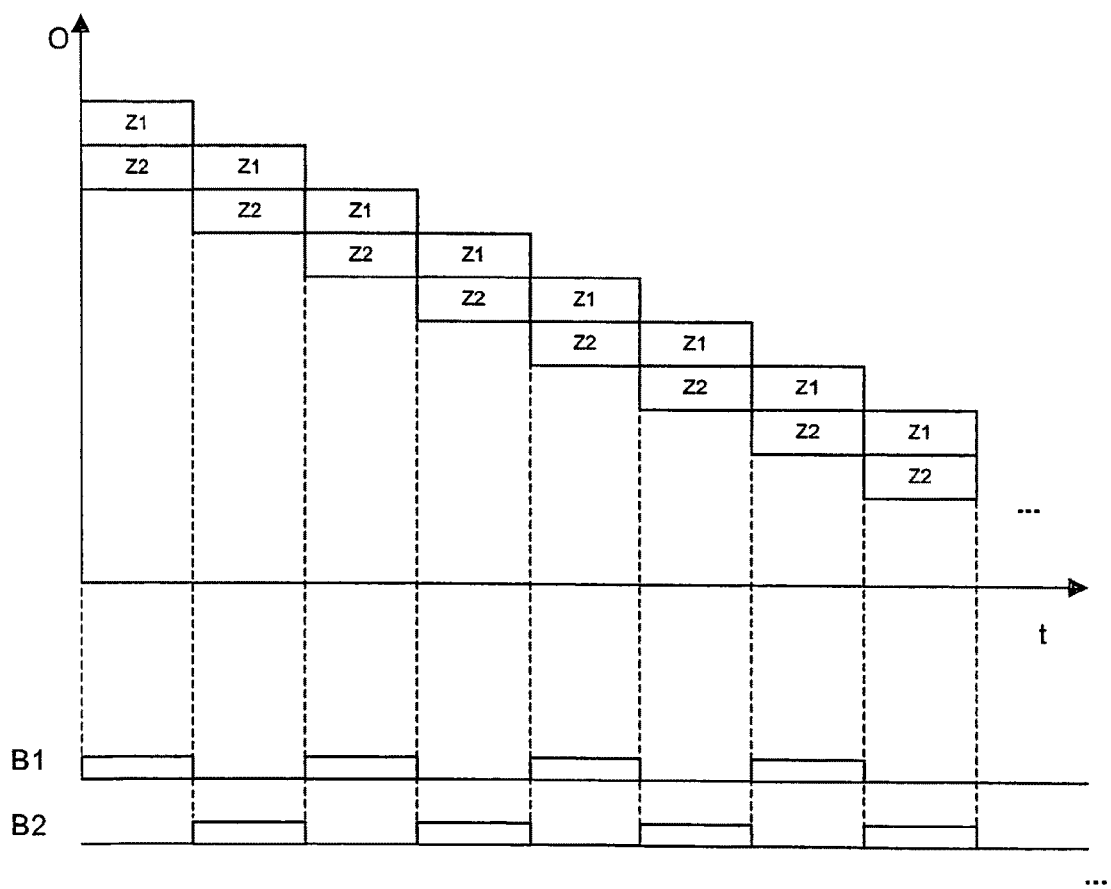
Figure 10C:
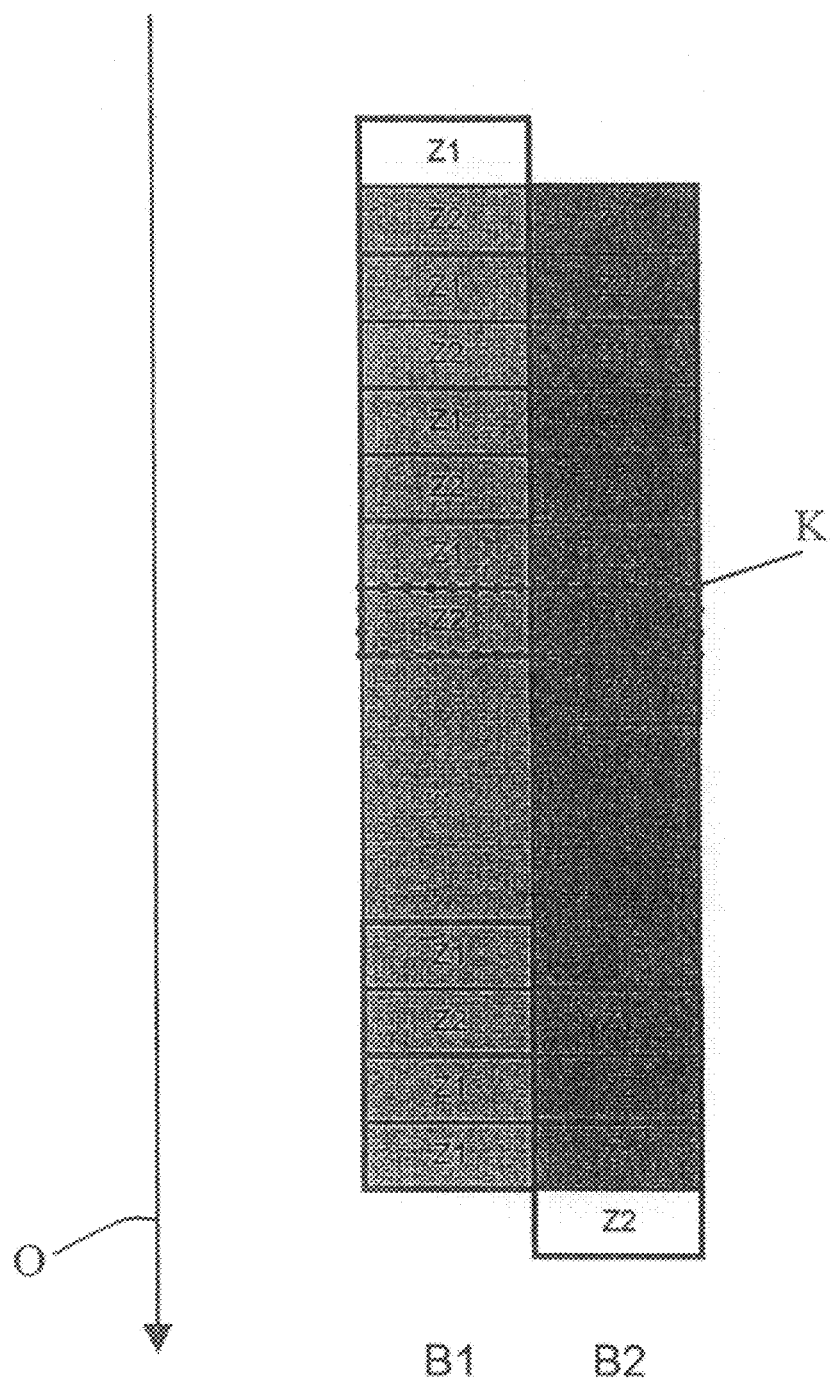
Figure 11A:
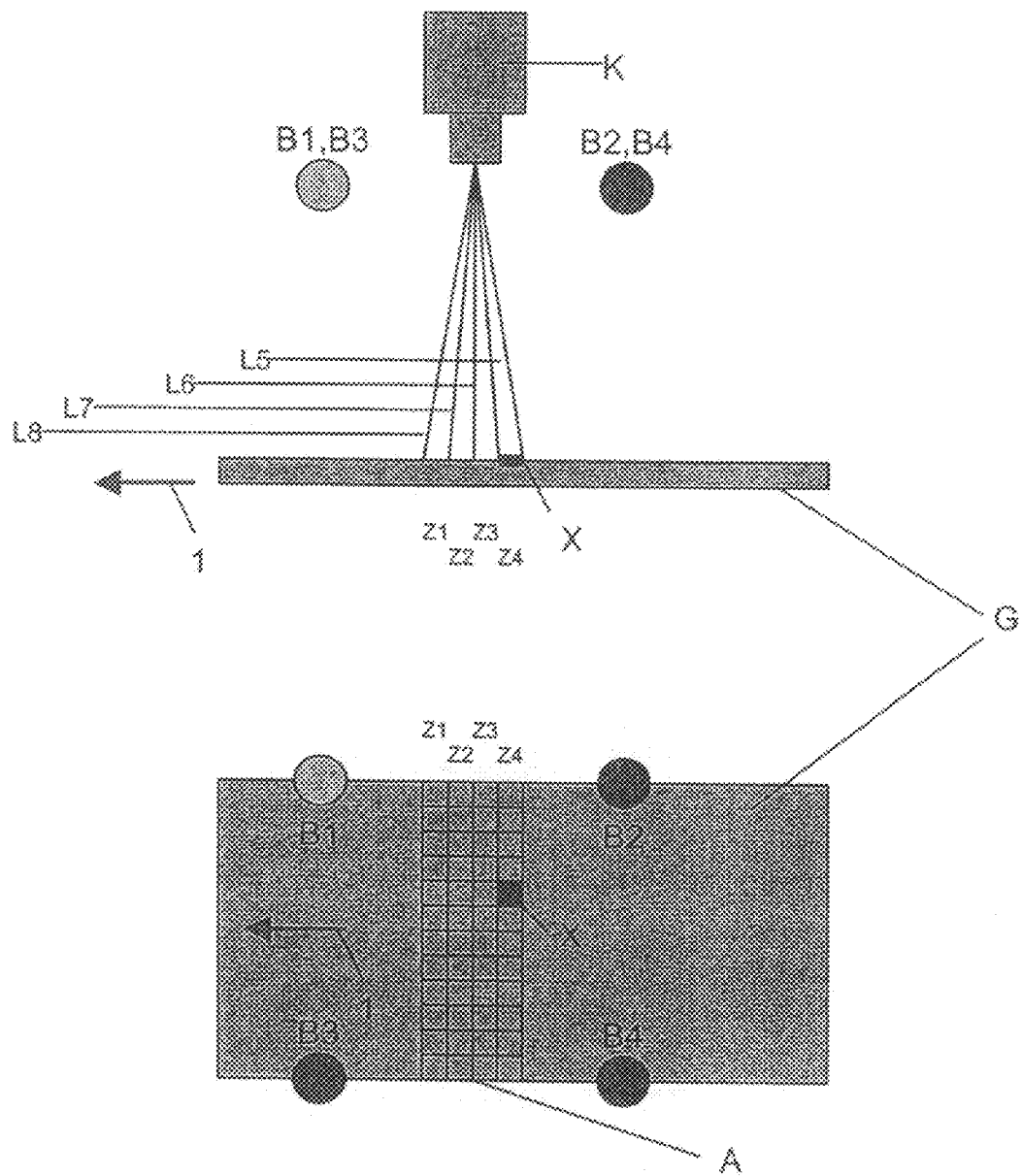
Figure 11B:
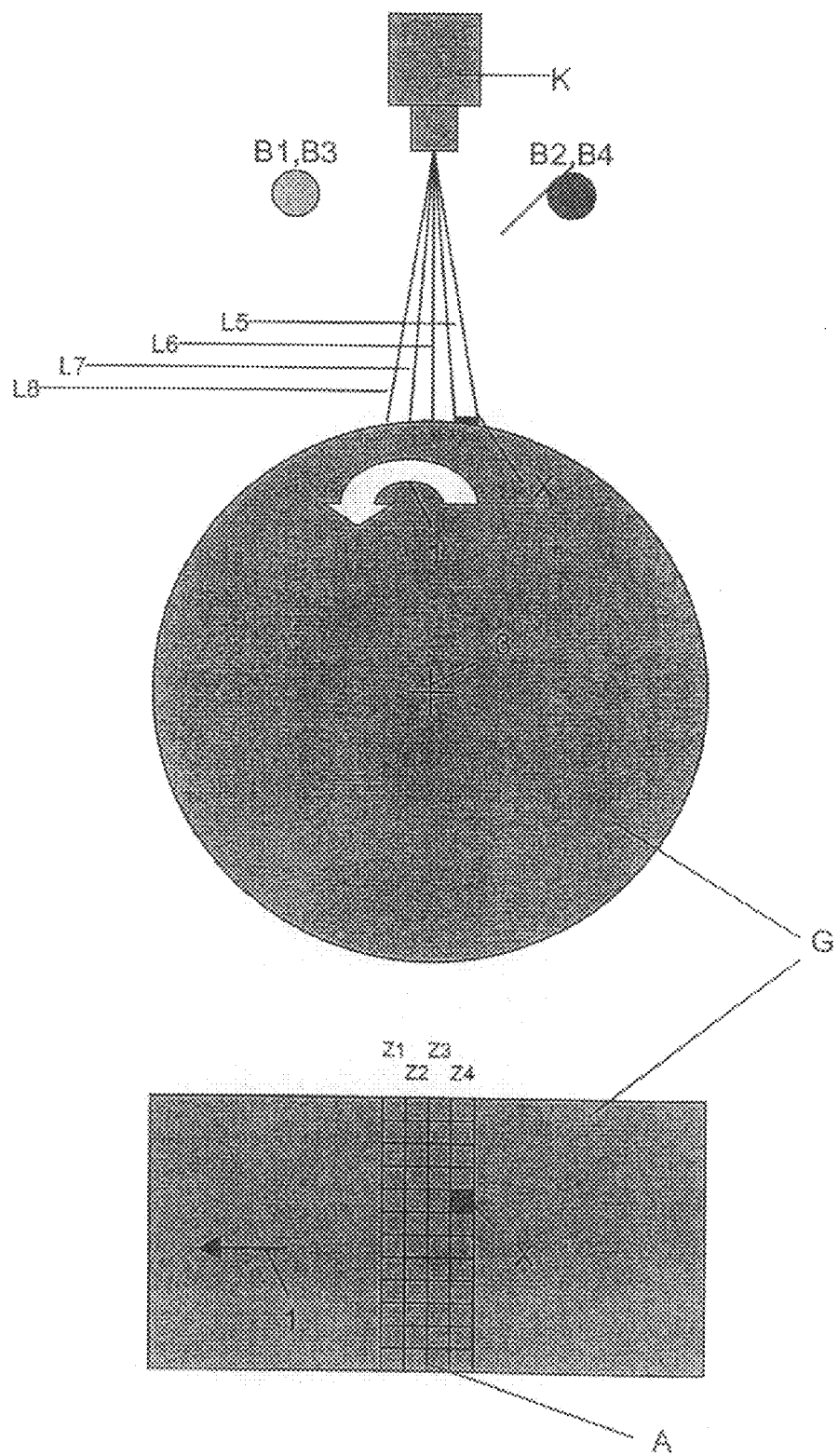
Figure 12A:
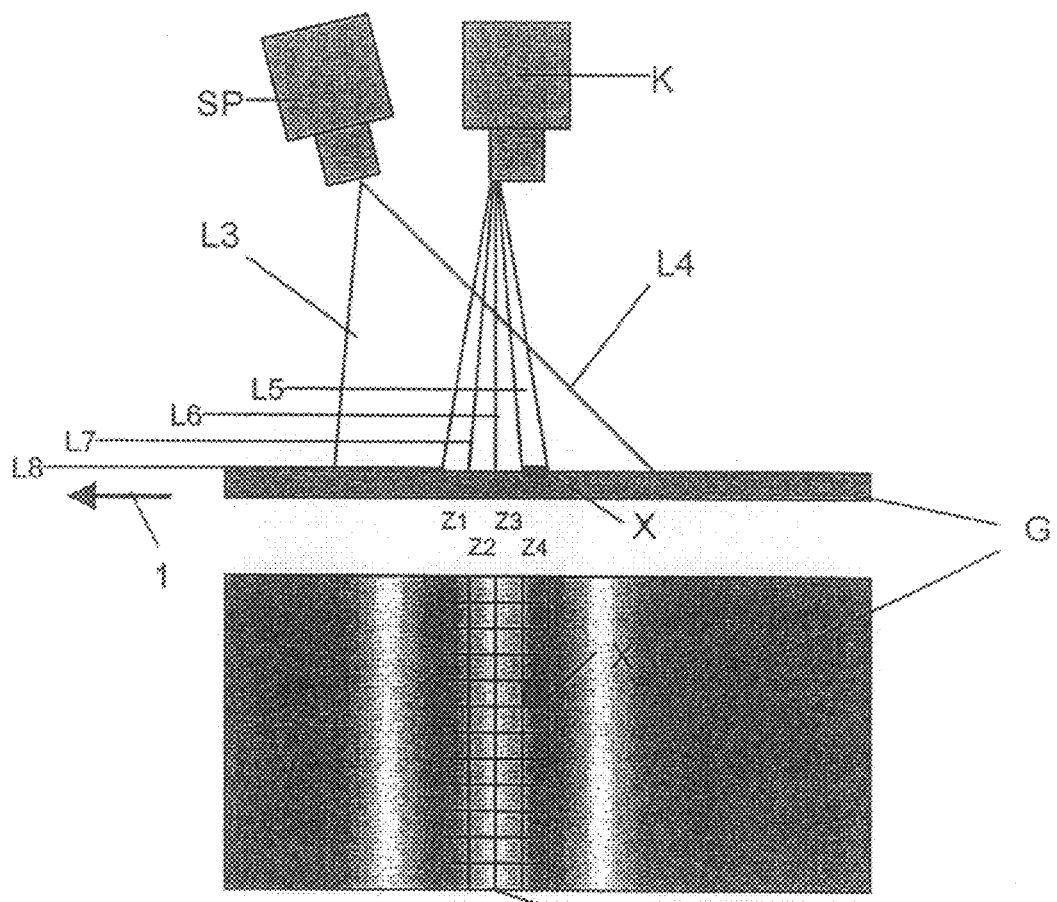
FIG. 12e shows the method according to the invention for application in stripe projection and a rotational movement by the test specimen G in the direction of the arrow 1 around the rotational axis 3. The same parts are designated using the same reference characters; in this regard, we refer to the preceding figures.
Figure 12B:
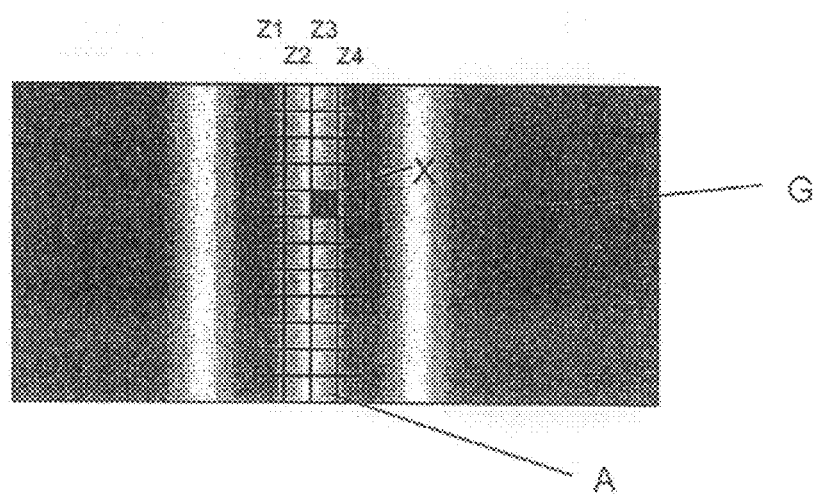
Figure 12C:
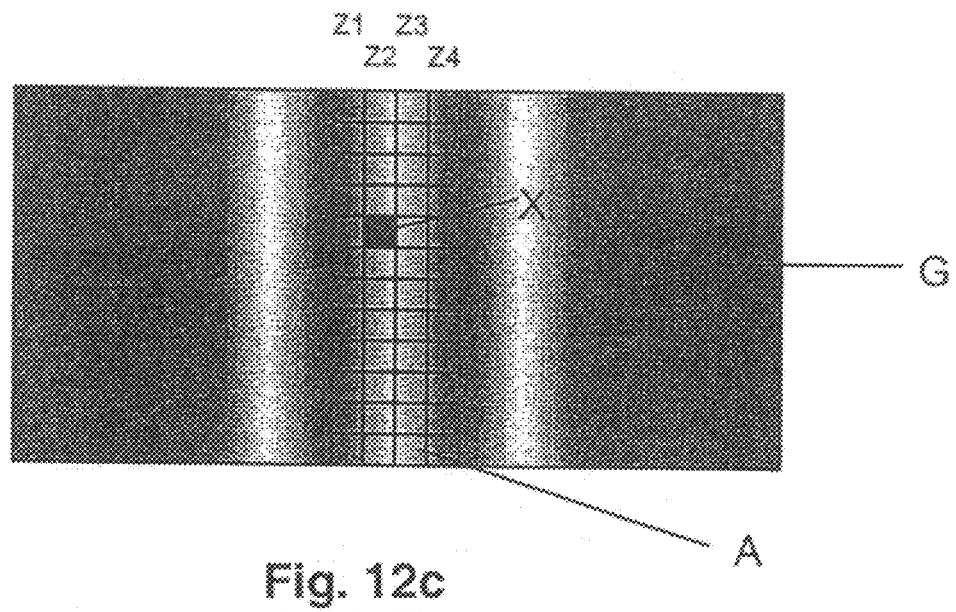
Figure 12D:
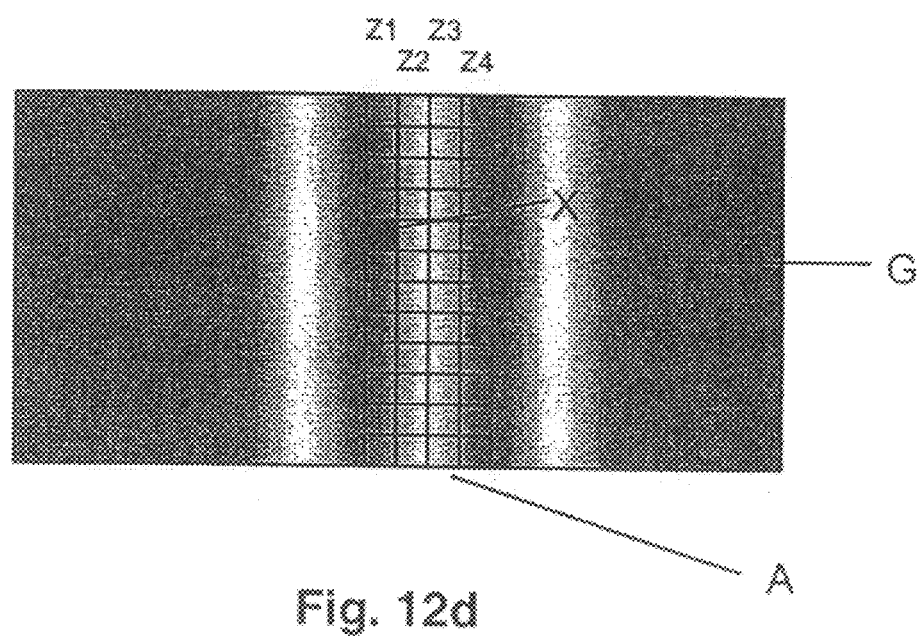
Figure 12E:
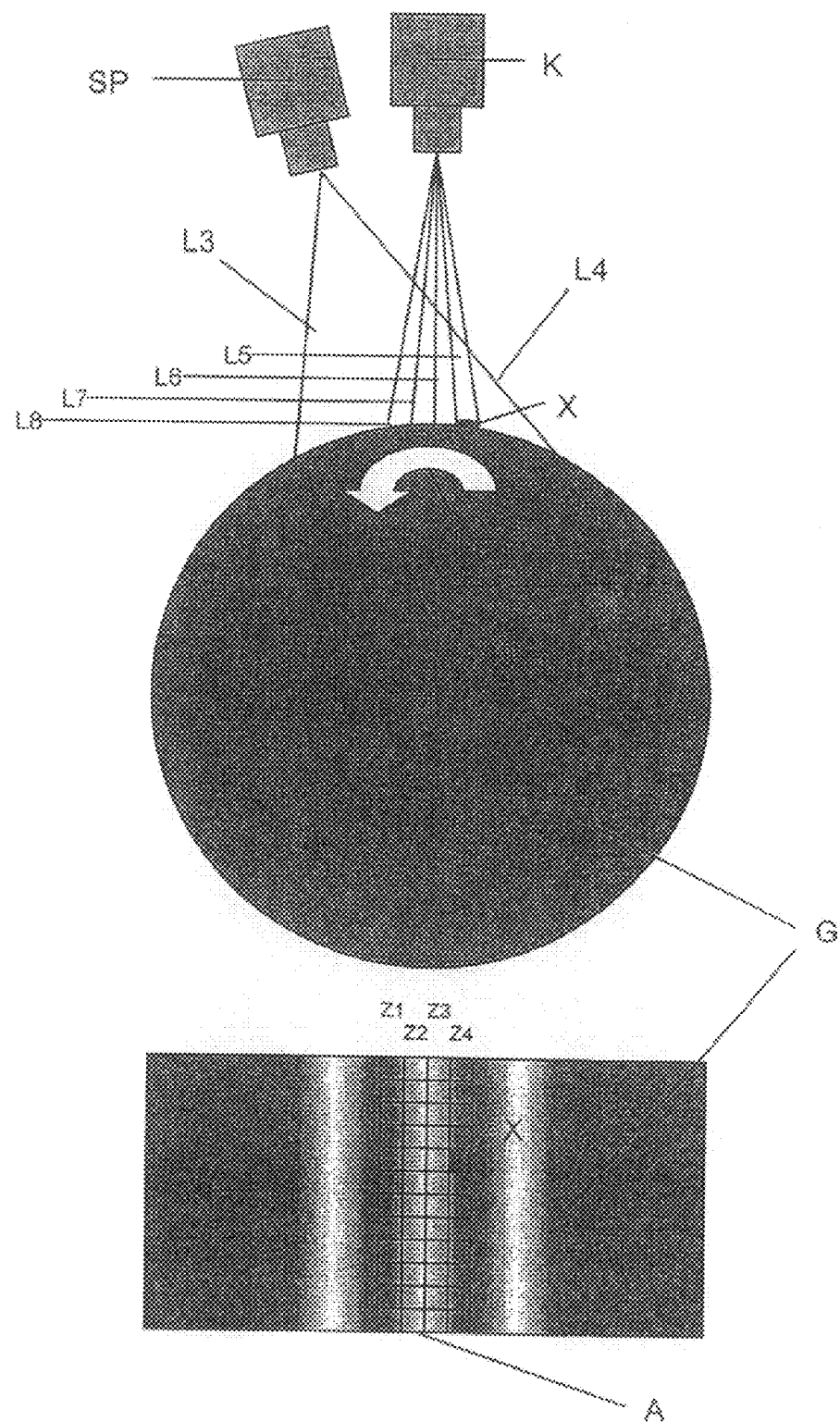

Such cameras with n=3 lines are available as color cameras. Here, every line is provided with its own color filter. Black and white cameras with three lines, which are also available, are even better suited for the method according to the invention. The special feature of such cameras can lie in the fact that the distance between neighboring lines is a multiple of the pixel distance within a line, for example, eight times. The test specimen may continue to move by the line distance from capture to capture, then the method according to the invention is to be performed as described. Advantageously, however, the test specimen continues to be moved only by one pixel distance from acquisition to acquisition. In this case, it is advantageous for n=3 illuminations to be actively connected for 8 captures before switching to the next illumination. This process is equivalent to 8n=24 lines being read in the case of a chip with a line distance corresponding to the pixel distance. The arrangement of the images in the memory may then occur advantageously analogously to FIG. 10a and 24 lines. Alternately, it is also possible for only n=2 of the three camera lines to be used. Then it is advantageous for the arrangement in the memory to correspond to FIG. 10a and 16 lines.

Additional cameras with a higher number of lines are available that include, for example, 96 or 100 lines. Such cameras are frequently used in accordance with the TDI (time delay integration) method. However many of these cameras may also be used as matrix cameras (area mode). These special cameras may be advantageously used for the method according to the invention, in particular when they are operated as matrix cameras. As a rule, the line distance here is equal or similar to the pixel distance that is common for other surface cameras.

Method for Multiple Matrix Cameras

Moreover, additional variants are conceivable in which standard matrix cameras with only one shutter S each are used and yet a short sequence of images over time is attained. For this purpose, a stereo arrangement of n cameras K1 to Kn is modified in such a way that they are able to fulfill this purpose. Here, the camera chips C of the cameras Kn are not exposed at the same time as is generally common, but rather with a slight temporal offset. According to the invention, this temporal offset is much shorter than would correspond to the refresh rate. This offset advantageously corresponds to the exposure duration of a camera chip C. The n illuminations B1 to Bn are controlled in such a way that a first illumination B1 occurs simultaneously with the exposure of the camera K1 with the shutter S1, the second illumination B2 with the exposure of the camera K2 with the shutter S2, up to the illumination Bn of the camera Kn with the shutter Sn. Alternately, it is possible for the illumination to be activated for less time than corresponds to the shutter time. Here as well, n=2 is a particularly interesting variant.

Directly after the exposure of the camera chip C of a camera Kn by an illumination Bn, the camera chip C of a next camera Kn is exposed with a next illumination Bn. This process repeats itself. Only after the exposure of a camera chip C of the camera Kn, a part of the camera chip C is read. Corresponding lines, i.e., lines of the various camera chips C that were acquired under various illumination situations, are arranged correspondingly in a memory taking into account of a disparity of the camera Kn.

Initially, this approach appears absurd because, in a stereo arrangement, an offset of the images from camera K1 to Kn exists, usually intentionally. From this offset, known as a disparity, the measurement signal is commonly attained, namely the spatial depth. Every variation of the disparity means a height difference of the object to be measured and is determined as precisely as possible. For the method according to the invention, the opposite is the case; here, the disparity is minimized as well as possible and kept constant. This is attained by virtue of the fact that the cameras are placed at as small a distance as possible from one another.

Figure 15:
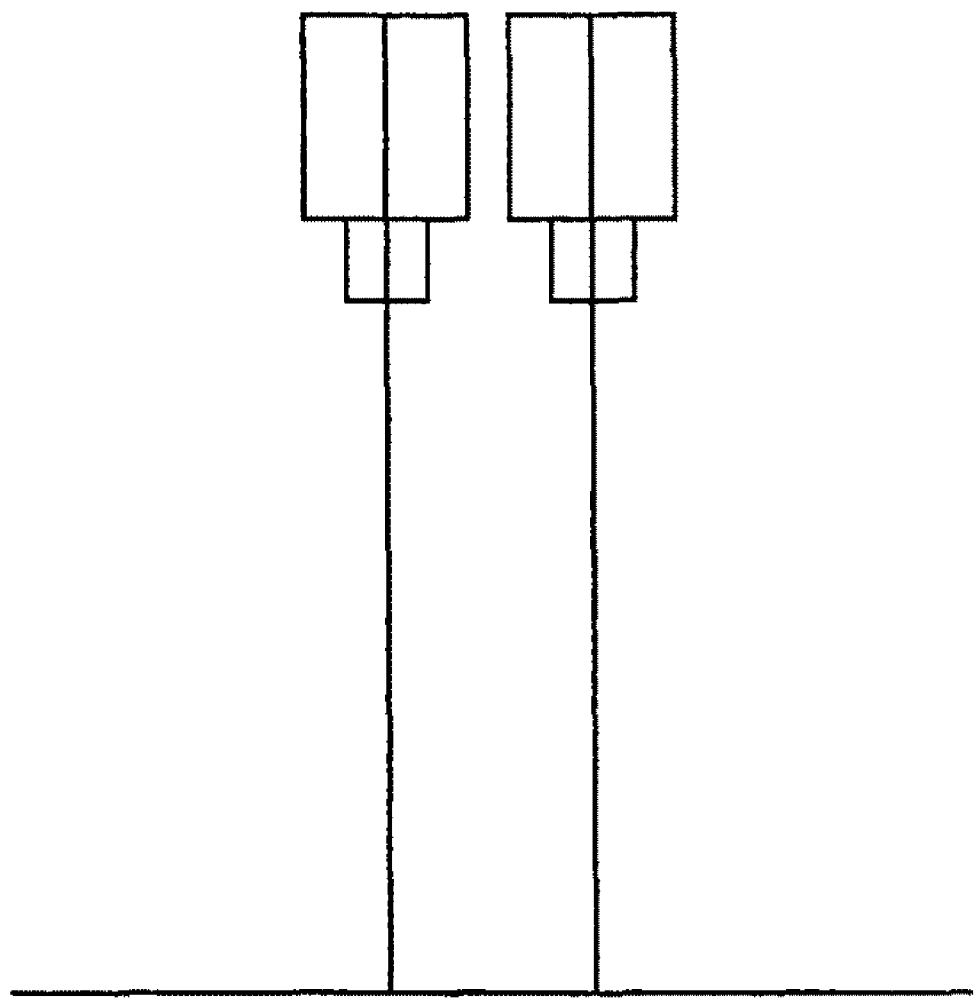

FIG. 15 describes a structure with two cameras K1 and K2. Preferably, both cameras are oriented with their optical axes parallel to one another. The test specimen G is positioned in a plane perpendicular to the optical axes of the cameras K1 and K2. It is particularly advantageous for the test specimen G to be guided always in this plane in an essentially even fashion and by a—preferably mechanical—device.

The disparity is then merely a constant offset by a certain number of pixel distances in all areas of the images. Preferably, the distance of the cameras is adjusted precisely in such a way that the disparity is a whole-number multiple of the pixel distance. Thus, it is possible to acquire corresponding pixels without interpolation. Alternately, the distance may be freely selected or the orientation of the camera axes may even be freely selected. In such cases, however, an interpolation is necessary in order to acquire corresponding pixels, i.e., pixels of the same location on surface of the test specimen.

If more than two cameras are used, they may be arranged in a row or even in a planar fashion. For example, four cameras may be placed in a square 2×2 arrangement, which minimizes distances. The special case for a disparity of zero may be achieved if two cameras are oriented in precisely the same manner on the test specimen G via a beam splitter.

Method for One Camera and Multiple Rotations

All of these variant solutions have in common that a series of images may be recorded with the smallest time delay, in particular when the object to be tested is in motion. For the particular case in which the test specimen G is rotating, for example, when the coating surface of a rotationally symmetrical test specimen should be captured, an additional alternative is possible: here, the test specimen G is scanned during its rotational movement by a line Z1 of a camera chip C while a first illumination B1 is active.

FIGS. 16a to 16d show an application of the method according to the invention with photometric deflectometry by way of example with four illuminations B1 to B4. The same parts are designated using the same reference characters; in this regard, we refer to the preceding figures.

In the upper portion of FIGS. 16a to 16d, a side view of the structure for photometric deflectometry is shown. The region L9 in the upper portion of FIGS. 16a to 16d designates the field of view of the line Z1 directed onto the test specimen G. The test specimen G rotates in the direction of the arrow 1 around the rotational axis 3. Moreover, a mark X is located on the rotating test specimen G. The respective light circles designate the active illumination.

The lower portion of FIGS. 16a to 16d depicts a top view of the structure without the camera K. A surface segment of the test specimen G is discernible onto which a line Z1 of the camera chip C of the camera K has been schematically projected, such that the synchronization between the illuminations B1 to B4 and the line Z1 may be shown.

Figure 16A:
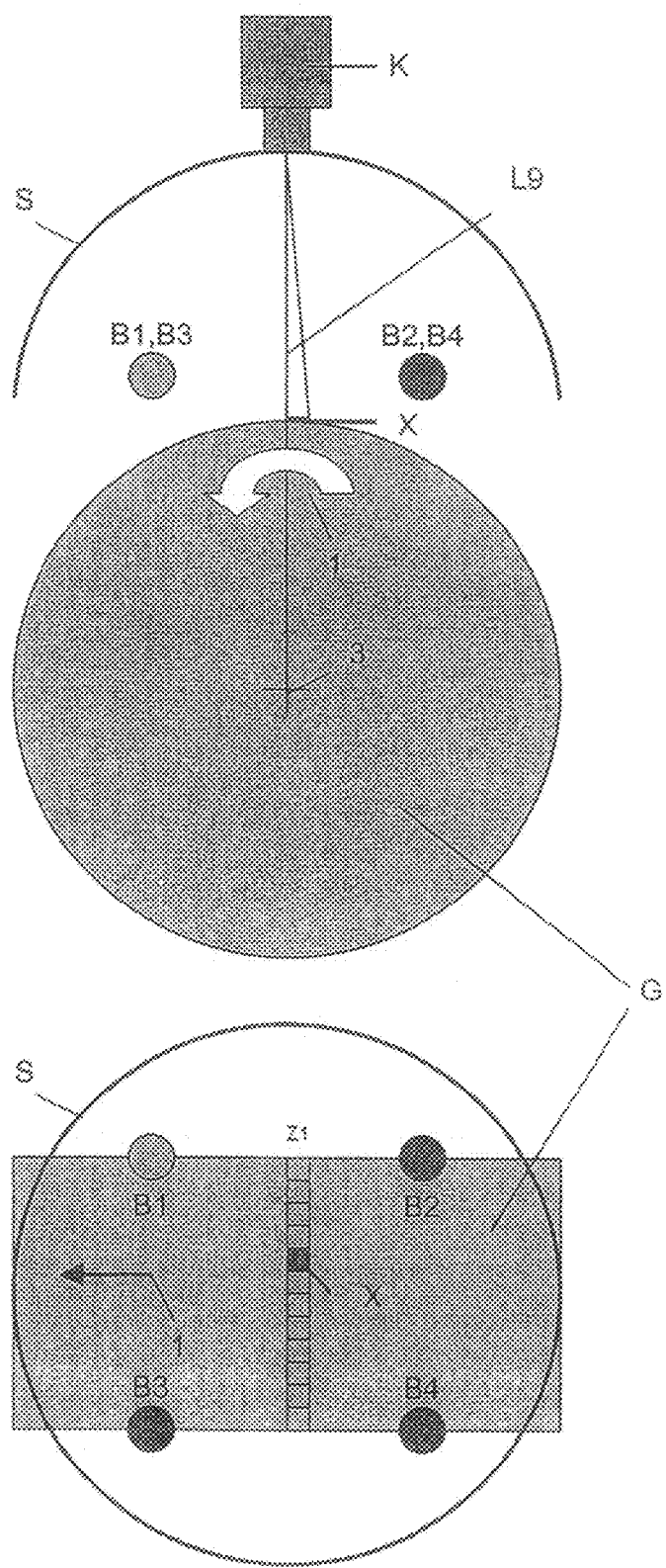
Figure 16B:
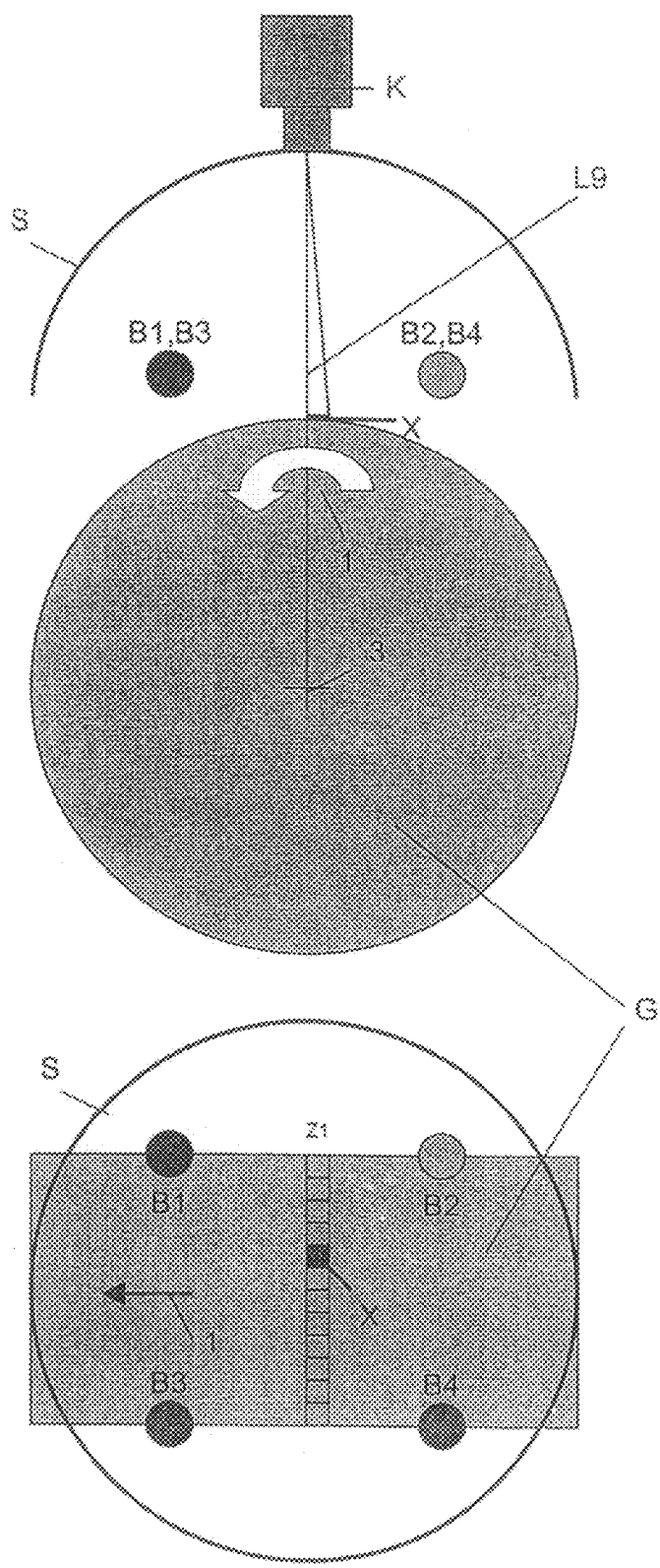
Figure 16C:
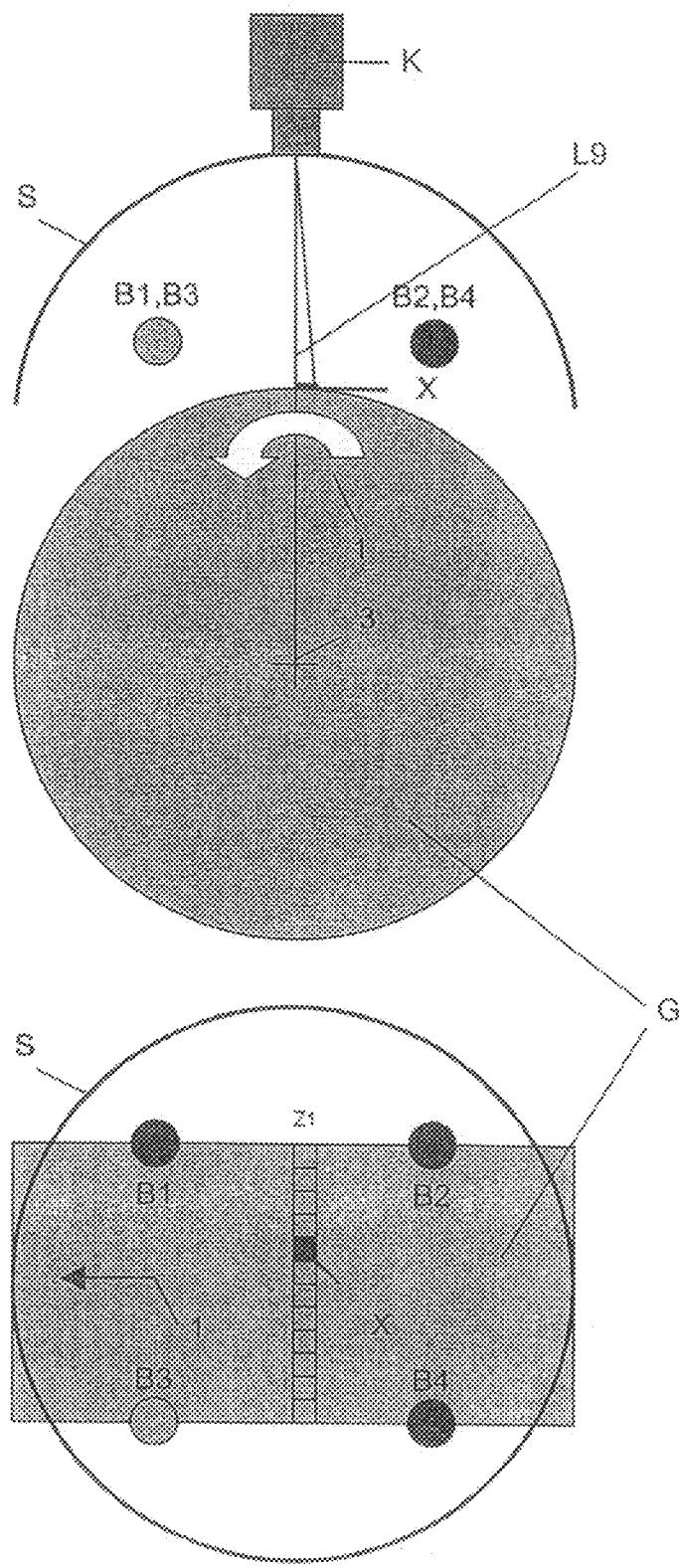
Figure 16D:
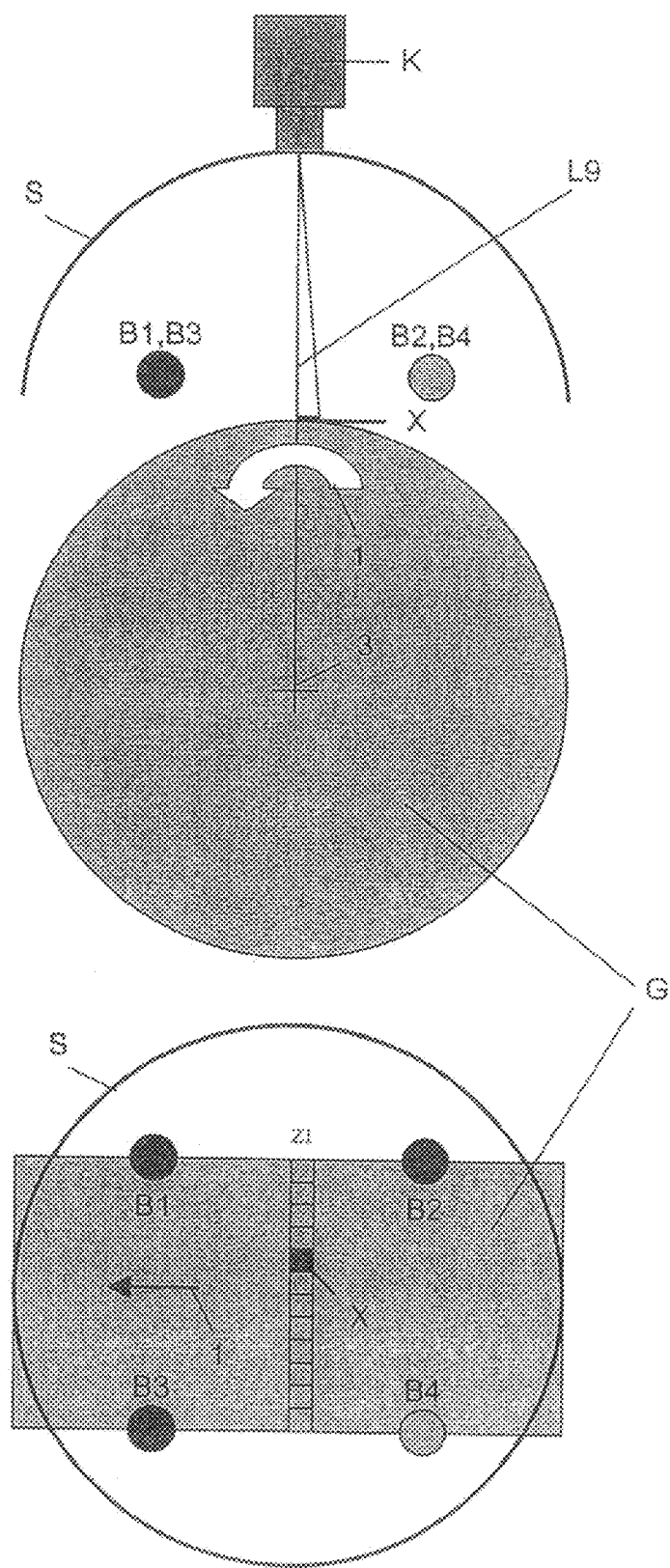

Other methods such as, for example, the photometric stereo method, stripe projection, and interferometric methods are also possible. As is shown in FIG. 16b, after a full rotation, the illumination B2 is activated instead of the illumination B1. After another rotation, the switch is made to the illumination B3 and, after yet another rotation, to the illumination B4, as is shown in FIGS. 16c and 16d. The desired number of illumination situations may vary. Here, it is important that, for every rotation, the individual lines be captured in a precisely congruent manner to the prior rotations. This may be achieved, for example, using a shaft encoder.

It is particularly advantageous if a line camera, but in particular a highly light-sensitive light camera, is used for the method according to the invention. Such a highly light-sensitive line camera, which is known per se, follows a mark X on the test specimen G over multiple lines by charge displacement and thus achieves a summation effect in exposure. This technique is known as TDI (time delay integration) technology.

Figure 16E:
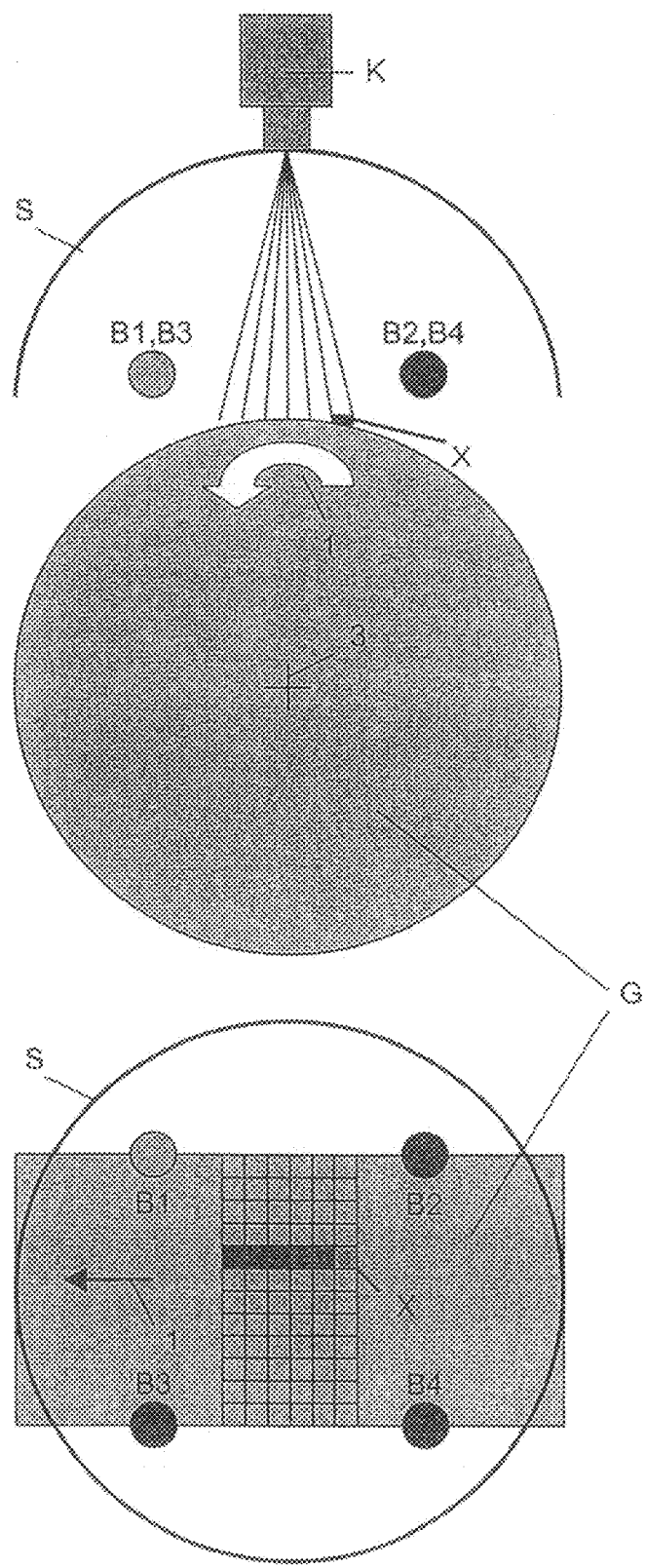

FIG. 16e shows the method according to the invention along with such a camera. In the lower portion of FIG. 16e, a line pattern of the camera chip C of the camera K is projected onto the test specimen G. The accumulation of loading from right to left is implied by an increasing grey shading. A particular advantage of this embodiment of the invention lies in the fact that the normally low amount of light in the case of line camera applications may typically be increased by a factor of 100 and, at the same time, the exposure time is reduced and a more rapid movement of the test specimen is made possible. In this manner, a drastic reduction in the capture and inspection time as well as in the capture and inspection costs is achieved.

The invention claimed is:

1. A method for recording a number of images of a test specimen in rotational motion with a camera using n different illuminations (B1 to Bn), the method comprising:
    activating the illumination for at least each full rotation of the rotating test specimen; and
    capturing with the camera the same point on the test specimen to be inspected for at least n complete rotations of the test specimen, wherein n>1.

2. The method according to claim 1, further comprising using a highly light-sensitive line camera.

3. The method according to claim 2, used in conjunction with a photometric deflectometry method.

4. The method according to claim 2, used in conjunction with a photometric stereo method.

5. The method according to claim 2, used in conjunction with a stripe projection method.

6. The method according to claim 2, used in conjunction with an interferometry method.

7. The method according to claim 2, used in conjunction with a white light interferometry method.

8. The method according to claim 2, used in conjunction with a stereo method.

* * * * *